(12) United States Patent
Woodage et al.

(10) Patent No.: US 6,905,855 B2
(45) Date of Patent: Jun. 14, 2005

(54) ISOLATED HUMAN DRUG-METABOLIZING PROTEINS, NUCLEIC ACID MOLECULES ENCODING HUMAN DRUG-METABOLIZING PROTEINS, AND USES THEREOF

(75) Inventors: Trevor Woodage, Washington, DC (US); Ming-Hui Wei, Germantown, MD (US); Chinnappa Kodira, Germantown, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 331 days.

(21) Appl. No.: 10/199,334

(22) Filed: Jul. 22, 2002

(65) Prior Publication Data
US 2003/0008354 A1 Jan. 9, 2003

Related U.S. Application Data

(62) Division of application No. 09/609,816, filed on Jul. 3, 2000, now Pat. No. 6,436,684.
(60) Provisional application No. 60/212,725, filed on Jun. 20, 2000, and provisional application No. 60/192,408, filed on Mar. 27, 2000.

(51) Int. Cl.[7] .......................... C12N 9/10; C12N 15/54; C12Q 1/68
(52) U.S. Cl. ...................... 435/193; 435/6; 435/252.3; 435/520.1; 435/536; 435/23.2
(58) Field of Search .............................. 435/193, 252.3, 435/6, 320.1; 536/23.2

*Primary Examiner*—Charles L. Patterson, Jr.
(74) *Attorney, Agent, or Firm*—Celera Genomics; Lin Sun-Hoffman

(57) ABSTRACT

The present invention provides amino acid sequences of peptides that are encoded by genes within the human genome, the proteins of the present invention. The present invention specifically provides isolated peptide and nucleic acid molecules, methods of identifying orthologs and paralogs of the proteins of the present invention, and methods of identifying modulators of the proteins of the present invention.

14 Claims, 16 Drawing Sheets

Transcript 1:
```
  1 ATTCCCAATG GCGAAGATTG AGAAAAACGC TCCCACGATG GAAAAAAAGC
 51 CAGAACTGTT TAACATCATG GAAGTAGATG GAGTCCCTAC GTTGATATTA
101 TCAAAAGAAT GGTGGGAAAA AGTATGTAAT TTCCAAGCCA AGCCTGATGA
151 TCTTATTCTG GCAACTTACC CAAAGTCAGG TACAACATGG ATGCATGAAA
201 TTTTAGACAT GATTCTAAAT GATGGTGATG TGGAGAAATG CAAAAGAGCC
251 CAGACTCTAG ATAGACACGC TTTCCTTGAA CTGAAATTTC CCCATAAAGA
301 AAAACCAGAT TTGGAGTTCG TTCTTGAAAT GTCCTCACCA CAACTGATAA
351 AAACACATCT CCCTTCACAT CTGATTCCAC CATCTATCTG GAAAGAAAAC
401 TGCAAGATTG TCTATGTGGC CAGAAATCCC AAGGATTGCC TGGTGTCCTA
451 CTACCACTTT CACAGGATGG CTTCCTTTAT GCCTGATCCT CAGAACTTAG
501 AGGAATTTTA TGAGAAATTC ATGTCCGGAA AAGTTGTTGG CGGGTCCTGG
551 TTTGACCATG TGAAAGGATG GTGGGCTGCA AAAGACATGC ACCGGATCCT
601 CTACCTCTTC TACGAGGATA TTAAAAAAAA TCCAAAACAT GAGATCCACA
651 AGGTGTTGGA ATTCTTGGAG AAAACTTGGT CAGGTGATGT TATAAACAAG
701 ATTGTCCACC ATACCTCATT TGATGTAATG AAGGATAATC CCATGGCCAA
751 CCATACTGCG GTACCTGCTC ACATATTCAA TCACTCCATC TCAAAATTTA
801 TGAGGAAAGG GATGCCTGGA GACTGGAAGA ACCACTTTAC TGTGGCTTTG
851 AATGAGAACT TTGATAAGCA TTATGAAAAG AAGATGGCAG GGTCCACACT
901 GAACTTCTGC CTGGAGATCT GAGAGGAACA ACAACAAACT AG
```
(SEQ ID NO:1)

FEATURES:
Start Codon: 8
Stop Codon: 920

Transcript 2:
```
  1 ATTCCCAATG GCGAAGATTG AGAAAAACGC TCCCACGATG GAAAAAAAGC
 51 CAGAACTGTT TAACATCATG GAAGTAGATG GAGTCCCTAC GTTGATATTA
101 TCAAAAGAAT GGTGGGAAAA AGTATGTAAT TTCCAAGCCA AGCCTGATGA
151 TCTTATTCTG GCAACTTACC CAAAGTCAGG TACAACATGG ATGCATGAAA
201 TTTTAGACAT GATTCTAAAT GATGGTGATG TGGAGAAATG CAAAAGAGCC
251 CAGACTCTAG ATAGACACGC TTTCCTTGAA CTGAAATTTC CCCATAAAGA
301 AAAACCAGAT TTGGAGTTCG TTCTTGAAAT GTCCTCACCA CAACTGATAA
351 AAACACATCT CCCTTCACAT CTGATTCCAC CATCTATCTG GAAAGAAAAC
401 TGCAAGATTG TCTATGTGGC CAGAAATCCC AAGGATTGCC TGGTGTCCTA
451 CTACCACTTT CACAGGATGG CTTCCTTTAT GCCTGATCCT CAGAACTTAG
501 AGGAATTTTA TGAGAAATTC ATGTCCGGAA AAGTTGTTGG CGGGTCCTGG
551 TTTGACCATG TGAAAGGATG GTGGGCTGCA AAAGACATGC ACCGGATCCT
601 CTACCTCTTC TACGAGGATA TTAAAAAAGA CCCAAAGCGG GAAATTGAGA
651 AGATACTGAA GTTCCTGGAA AAAGACATAT CAGAGGAAAT TCTGAATAAA
701 ATCATCTATC ACACCTCCTT TGATGTAATG AAGCAAAACC CAATGACCAA
751 CTATACCACT TTGCCCACCA GCATTATGGA CCACTCCATC TCCCCTTTTA
801 TGAGGAAAGG GATGCCTGGA GACTGGAAGA ACTATTTTAC TGTGGCCCAA
851 AATGAAGAAT TTGACAAGGA CTACCAGAAG AAGATGGCAG GAAGCACCCT
901 AACCTTCCGC ACAGAGATCT GA
```
(SEQ ID NO:2)

FEATURES:
Start: 8
Stop: 920

FIGURE 1A cDNA sequence
```
   1 CTCACTATTA GGGCGAATTG AATTTAGCGG CCGCGAATTC GCCCTTATGG
  51 CGAAGATTGA GAAAAACGCT CCCACGATGG AAAAAAAGCC AGAACTGTTT
 101 AACATCATGG AAGTAGATGG AGTCCCTACG TTGATATTAT CAAAAGAATG
 151 GTGGGAAAAA GTCTGTAATT TCCAAGCCAA GCCTGATGAT CTTATTCTGG
 201 CAACTTACCC AAAGTCAGGT ACAACATGGA TGCATGAAAT TTTAGACATG
 251 ATTCTAAATG ATGGTGATGT GGAGAAATGC AAAAGAGCCC AGACTCTAGA
 301 TAGACACGCT TTCCTTGAAC TGAAATTTCC CCATAAAGAA AAACCAGATT
 351 TGGAGTTCGT TCTTGAAATG TCCTCACCAC AACTGATAAA AACACATCTC
 401 CCTTCACATC TGATTCCACC ATCTATCTGG AAAGAAAACT GCAAGATTGT
 451 CTATGTGGCC AGAAATCCCA AGGATTGCCT GGTGTCCTAC TACCACTTTC
 501 ACAGGATGGC TTCCTTTATG CCTGATCCTC AGAACTTAGA GGAATTTTAT
 551 GAGAAATTCA TGTCCGGAAA AGTTGTTGGC GGGTCCTGGT TTGACCATGT
 601 GAAAGGATGG TGGGCTGCAA AAGACACGCA CCGGATCCTC TACCTCTTCT
 651 ACGAGGATAT TAAAAAAAAT CCAAAACATG AGATCCACAA GGTGTTGGAA
 701 TTCTTGGAGA AAACTTTGTC AGGTGATGTT ATAAACAAGA TTGTCCACCA
 751 TACCTCATTT GATGTAATGA AGGATAATCC CATGGCCAAC CATACTGCGG
 801 TACCTGCTCA CATATTCAAT CACTCCATCT CAAAATTTAT GAGGAAAGGG
 851 ATGCCTGGAG ACTGGAAGAA CCACTTTACT GTGGCTATGA ATGAGAACTT
 901 TGATAAGCAT TATGAAAAGA AGATGGCAGG GTCCACACTG AACTTCTGCC
 951 TGGAGATCTG AGAGGAACAA CAAAGGGCGA ATTCGTTTAA ACCTGCAGGA
1001 CTAG
```
(SEQ ID NO:3)

FEATURES:
5'UTR: 1-47
Start: 47
Stop: 959
3'UTR: 959-1004

Homologous proteins:
Top 10 BLAST Hits

|  | Score | E |
|---|---|---|
| gi\|1711569\|sp\|P50237\|SUAC_RAT N-HYDROXYARYLAMINE SULFOTRANSFERA... | 388 | e-107 |
| gi\|3004922\|gb\|AAC17740.1\| (AF033653) phenol sulfotransferase [M... | 388 | e-107 |
| gi\|8117877\|gb\|AAF72810.1\|AF186263_1 (AF186263) sulfotransferase... | 360 | 2e-98 |
| gi\|5730071\|ref\|NP_006579.1\| SULT1C sulfotransferase >gi\|3649608... | 360 | 2e-98 |
| gi\|4507305\|ref\|NP_001047.1\| sulfotransferase family 1C, member ... | 348 | 4e-95 |
| gi\|4689040\|emb\|CAB41460.1\| (AJ238391) sulfotransferase K1 [Ratt... | 344 | 6e-94 |
| gi\|2828826\|gb\|AAC00410.1\| (AF026304) sulfotransferase [Oryctola... | 340 | 1e-92 |
| gi\|4689042\|emb\|CAB41461.1\| (AJ238392) sulfotransferase K2 [Ratt... | 338 | 6e-92 |
| gi\|2290540\|gb\|AAB65154.1\| (U95726) thyroid hormone sulfotransfe... | 332 | 3e-90 |
| gi\|4096440\|gb\|AAC99889.1\| (U32371) tyrosine-ester sulfotransfer... | 332 | 4e-90 |
| gi\|7657621\|ref\|NP_055280.1\| thyroid hormone slfotransferase >gi... | 332 | 4e-90 |
| gi\|7949146\|ref\|NP_058051.1\| amine N-sulfotransferase >gi\|743496... | 329 | 3e-89 |
| gi\|8117857\|gb\|AAF72802.1\|AF186254_1 (AF186254) sulfotransferase... | 328 | 6e-89 |

EXPRESSION INFORMATION FOR MODULATORY USE:
library source for cDNA:
Human Kidney
Human Small Intestine

FIGURE 1B

Protein 1 (from Transcript 1):

```
  1 MAKIEKNAPT MEKKPELFNI MEVDGVPTLI LSKEWWEKVC NFQAKPDDLI
 51 LATYPKSGTT WMHEILDMIL NDGDVEKCKR AQTLDRHAFL ELKFPHKEKP
101 DLEFVLEMSS PQLIKTHLPS HLIPPSIWKE NCKIVYVARN PKDCLVSYYH
151 FHRMASFMPD PQNLEEFYEK FMSGKVVGGS WFDHVKGWWA AKDMHRILYL
201 FYEDIKKNPK HEIHKVLEFL EKTWSGDVIN KIVHHTSFDV MKDNPMANHT
251 AVPAHIFNHS ISKFMRKGMP GDWKNHFTVA LNENFDKHYE KKMAGSTLNF
301 CLEI
```
(SEQ ID NO:4)

Features
Hmmer Results:
Scores for sequence family classification (score includes all domains):

| Model | Description | Score | E-value | N |
|---|---|---|---|---|
| PF00685 | Sulfotransferase proteins | 512.4 | 3.2e-150 | 1 |

Parsed for domains:

| Model | Domain | seq-f | seq-t | hmm-f | hmm-t | score | E-value |
|---|---|---|---|---|---|---|---|
| PF00685 | 1/1 | 24 | 292 .. | 1 | 281 [] | 512.4 | 3.2e-150 |

Important Domains
Prosite search results:
[1] PDOC00001 PS00001 ASN_GLYCOSYLATION
N-glycosylation site
Number of matches: 2
    1    248-251 NHTA
    2    258-261 NHSI

[2] PDOC00005 PS00005 PKC_PHOSPHO_SITE
Protein kinase C phosphorylation site
        173-175 SGK

[3] PDOC00006 PS00006 CK2_PHOSPHO_SITE
Casein kinase II phosphorylation site
Number of matches: 2
    1    180-183 SWFD
    2    236-239 TSFD

[4] PDOC00008 PS00008 MYRISTYL
N-myristoylation site
        295-300 GSTLNF

FIGURE 2A

Alignment to Top Blast Hit:
>gi|1711569|sp|P50237|SUAC_RAT N-HYDROXYARYLAMINE SULFOTRANSFERASE
    (HAST-I) >gi|543420|pir||A49098 N-hydroxyarylamine
    sulfotransferase, HAST-I - rat >gi|440841|gb|AAA42181.1|
    (L22339) N-hydroxy-2-acetylaminofluorene [Rattus
    norvegicus]
    Length = 304

Score = 388 bits (987), Expect = e-107
Identities = 174/283 (61%), Positives = 220/283 (77%)
Frame = +2

```
Query: 71  EVDGVPTLILSKEWWEKVCNFQAKPDDLILATYPKSGTTWMHEILDMILNDGDVEKCKRA 250
           EV+G+    L + W+K+ NFQAKPDDL++ATY K+GTTW  EI+DMI NDGDV+KC+RA
Sbjct: 22  EVNGILMSKLMSDNWDKIWNFQAKPDDLLIATYAKAGTTWTQEIVDMIQNDGDVQKCQRA 81

Query: 251 QTLDRHAFLELKFPHKEKPDLEFVLEMSSPQLIKTHLPSHLIPPSIWKENCKIVYVARNP 430
           T DRH F+E  P    L+   +M SP+ +KTHLP HH++PPS WKEN KI+YVARN
Sbjct: 82  NTYDRHPFIEWTLPSPLNSGLDLANKMPSPRTLKTHLPVHMLPPSFWKENSKIIYVARNA 141

Query: 431 KDCLVSYYHFHRMASFMPDPQNLEEFYEKFMSGKVVGGSWFDHVKGWWAAKDMHRILYLF 610
           KDCLVSYY+F  RM   +PDP  L E+ E+F +GKV+ GSW+DHVKGWW  KD HRILYLF
Sbjct: 142 KDCLVSYYYFSRMNKMLPDPGTLGEYIEQFKAGKVLWGSWYDHVKGWWDVKDQHRILYLF 201

Query: 611 YEDIKKNPKHEIHKVLEFLEKTWSGDVINKIVHHTSFDVMKDNPMANHTAVPAHIFNHSI 790
           YED+K++PK EI K+ +FLEK S +V+NKI++HTSFDVMK+NPMAN+T +P+ I +HSI
Sbjct: 202 YEDMKEDPKREIKKIAKFLEKDISEEVLNKIIYHTSFDVMKENPMANYTTLPSSIMDHSI 261

Query: 791 SKFMRKGMPGDWKNHFTVALNENFDKHYEKKMAGSTLNFCLEI 919
           S FMRKGMPGDWKN+FTVA +E+FD+ Y +KMAGS + F  EI
Sbjct: 262 SPFMRKGMPGDWKNYFTVAQSEDFDEDYRRKMAGSNITFRTEI 304
```
(SEQ ID NO: 8)

Membrane Spanning Regions:
None found

Protein 2 (from Transcript 2):
```
  1 MAKIEKNAPT MEKKPELFNI MEVDGVPTLI LSKEWWEKVC NFQAKPDDLI
 51 LATYPKSGTT WMHEILDMIL NDGDVEKCKR AQTLDRHAFL ELKFPHKEKP
101 DLEFVLEMSS PQLIKTHLPS HLIPPSIWKE NCKIVYVARN PKDCLVSYYH
151 FHRMASFMPD PQNLEEFYEK FMSGKVVGGS WFDHVKGWWA AKDMHRILYL
201 FYEDIKKDPK REIEKILKFL EKDISEEILN KIIYHTSFDV MKQNPMTNYT
251 TLPTSIMDHS ISPFMRKGMP GDWKNYFTVA QNEEFDKDYQ KKMAGSTLTF
301 RTEI
```
(SEQ ID NO:5)

Features:
  Hmmer Results:
  Scores for sequence family classification (score includes all domains):
  Model     Description                                    Score    E-value   N
  --------  -----------                                    -----    -------  ---
  PF00685   Sulfotransferase proteins                      550.5    1.2e-161  1
  Parsed for domains:
  Model     Domain  seq-f  seq-t    hmm-f  hmm-t     score  E-value
  --------  ------  -----  -----    -----  -----     -----  -------
  PF00685    1/1      24    292  ..      1    281 []  550.5  1.2e-161

Membrane Spanning Regions:
None found

FIGURE 2B

Important Domains:
  Prosite search results:
[1] PDOC00001 PS00001 ASN_GLYCOSYLATION
N-glycosylation site
       248-251 NYTT

[2] PDOC00005 PS00005 PKC_PHOSPHO_SITE
Protein kinase C phosphorylation site
Number of matches: 2
    1    173-175 SGK
    2    299-301 TFR

[3] PDOC00006 PS00006 CK2_PHOSPHO_SITE
Casein kinase II phosphorylation site
Number of matches: 3
    1    180-183 SWFD
    2    236-239 TSFD
    3    255-258 SIMD

[4] PDOC00008 PS00008 MYRISTYL
N-myristoylation site
       295-300 GSTLTF

Alignment to Top Blast Hit:
>gi|1711569|sp|P50237|SUAC_RAT N-HYDROXYARYLAMINE SULFOTRANSFERASE
       (HAST-I) >gi|543420|pir||A49098 N-hydroxyarylamine
       sulfotransferase, HAST-I - rat >gi|440841|gb|AAA42181.1|
       (L22339) N-hydroxy-2-acetylaminofluorene [Rattus
       norvegicus]
       Length = 304

Score = 435 bits (1107), Expect = e-121
 Identities = 196/283 (69%), Positives = 234/283 (82%)
 Frame = +2
Query: 71   EVDGVPTLILSKEWWEKVCNFQAKPDDLILATYPKSGTTWMHEILDMILNDGDVEKCKRA 250
            EV+G+     L  + W+K+ NFQAKPDDL++ATY K+GTTW   EI+DMI NDGDV+KC+RA
Sbjct: 22   EVNGILMSKLMSDNWDKIWNFQAKPDDLLIATYAKAGTTWTQEIVDMIQNDGDVQKCQRA 81
Query: 251  QTLDRHAFLELKFPHKEKPDLEFVLEMSSPQLIKTHLPSHLIPPSIWKENCKIVYVARNP 430
             T DRH F+E P      L+    +M SP+ +KTHLP H++PPS WKEN KI+YVARN
Sbjct: 82   NTYDRHPFIEWTLPSPLNSGLDLANKMPSPRTLKTHLPVHMLPPSFWKENSKIITYVARNA 141
Query: 431  KDCLVSYYHFHRMASFMPDPQNLEEFYEKFMSGKVVGGSWFDHVKGWWAAKDMHRILYLF 610
            KDCLVSYY+F RM  +PDP L E+ E+F +GKV+ GSW+DHVKGWW  KD HRILYLF
Sbjct: 142  KDCLVSYYYFSRMNKMLPDPGTLGEYIEQFKAGKVLWGSWYDHVKGWWDVKDQHRILYLF 201
Query: 611  YEDIKKDPKREIEKILKFLEKDISEEILNKIIYHTSFDVMKQNPMTNYTTLPTSIMDHSI 790
            YED+K+DPKREI+KI KFLEKDISEE+LNKIIYHTSFDVMK+NPM NYTTLP+SIMDHSI
Sbjct: 202  YEDMKEDPKREIKKIAKFLEKDISEEVLNKIIYHTSFDVMKENPMANYTTLPSSIMDHSI 261
Query: 791  SPFMRKGMPGDWKNYFTVAQNEEFDKDYQKKMAGSTLTFRTEI 919
            SPFMRKGMPGDWKNYFTVAQ+E+FD+DY++KMAGS +TFRTEI
Sbjct: 262  SPFMRKGMPGDWKNYFTVAQSEDFDEDYRRKMAGSNITFRTEI 304
(SEQ ID NO: 9)

FIGURE 2C

Protein 3 (from cDNA):
```
  1 MAKIEKNAPT MEKKPELFNI MEVDGVPTLI LSKEWWEKVC NFQAKPDDLI
 51 LATYPKSGTT WMHEILDMIL NDGDVEKCKR AQTLDRHAFL ELKFPHKEKP
101 DLEFVLEMSS PQLIKTHLPS HLIPPSIWKE NCKIVYVARN PKDCLVSYYH
151 FHRMASFMPD PQNLEEFYEK FMSGKVVGGS WFDHVKGWWA AKDTHRILYL
201 FYEDIKKNPK HEIHKVLEFL EKTLSGDVIN KIVHHTSFDV MKDNPMANHT
251 AVPAHIFNHS ISKFMRKGMP GDWKNHFTVA MNENFDKHYE KKMAGSTLNF
301 CLEI
```
(SEQ ID NO:6)

Features:
Alignment to Top Blast Hit:
>gi|3004922|gb|AAC17740.1| (AF033653) phenol sulfotransferase [Mus
    musculus]
    Length = 304

Score = 391 bits (993), Expect = e-108
Identities = 175/283 (61%), Positives = 220/283 (76%)
```
Query:  22 EVDGVPTLILSKEWWEKVCNFQAKPDDLILATYPKSGTTWMHEILDMILNDGDVEKCKRA 81
            EV+G+   + E W+K+ NFQAKPDDL++ATY K+GTTW  EI+DMI NDGDV+KC+RA
Sbjct:  22 EVNGILMSKMMSENWDKIWNFQAKPDDLLIATYAKAGTTWTQEIVDMIQNDGDVQKCQRA 81
Query:  82 QTLDRHAFLELKFPHKEKPDLEFVLEMSSPQLIKTHLPSHLIPPSIWKENCKIVYVARNP 141
             T DRH F+E   P     L+   +M SP+ +KTHLP  ++PPS WKEN +I+YVARN
Sbjct:  82 NTYDRHPFIEWTLPPPLNSGLDLANKMPSPRTLKTHLPVQMLPPSFWKENSQIIYVARNA 141
Query: 142 KDCLVSYYHFHRMASFMPDPQNLEEFYEKFMSGKVVGGSWFDHVKGWWAAKDTHRILYLF 201
            KDCLVSYY+F RM   +PDP  L E+ E F +GKV+ GSW+DHVKGWW  KD HRILYLF
Sbjct: 142 KDCLVSYYYFSRMNKMLPDPGTLGEYIETFKAGKVLWGSWYDHVKGWWDVKDKHRILYLF 201
Query: 202 YEDIKKNPKHEIHKVLEFLEKTLSGDVINKIVHHTSFDVMKDNPMANHTAVPAHIFNHSI 261
            YED+K++PK EI K+++FLEK +S +V+NKI+HHTSFDVMK NPMAN+T +P+ I +HSI
Sbjct: 202 YEDMKEDPKREIKKIVKFLEKDISEEVLNKIIHHTSFDVMKQNPMANYTTLPSSIMDHSI 261
Query: 262 SKFMRKGMPGDWKNHFTVAMNENFDKHYEKKMAGSTLNFCLEI 304
            S FMRKGMPGDWKN+FTVA +E+FD+ Y KKMAGST+ F EI
Sbjct: 262 SPFMRKGMPGDWKNYFTVAQSEDFDEDYRKKMAGSTITFRTEI 304
```
(SEQ ID NO: 10)

Membrane Spanning Regions:
None found

Important Domains:
Prosite:
[1] PDOC00001 PS00001 ASN_GLYCOSYLATIONN-glycosylation site
Number of matches: 2
    1   248-251 NHTA
    2   258-261 NHSI
------------------------------------------------------------[2]
PDOC00005 PS00005 PKC_PHOSPHO_SITEProtein kinase C phosphorylation site
Number of matches: 2
    1   173-175 SGK
    2   194-196 THR
------------------------------------------------------------[3]
PDOC00006 PS00006 CK2_PHOSPHO_SITECasein kinase II phosphorylation site
Number of matches: 2
    1   180-183 SWFD
    2   236-239 TSFD

FIGURE 2D

```
------------------------------------------------------------------------------[4]
PDOC00008 PS00008 MYRISTYLN-myristoylation site
          295-300 GSTLNF Hmmer:
Scores for sequence family classification (score includes all domains):
Model    Description                                    Score    E-value   N
-------  -----------                                    -----    -------  ---
PF00685  Sulfotransferase proteins                      518.6    4.7e-152  1
Parsed for domains:
Model    Domain  seq-f seq-t    hmm-f hmm-t    score  E-value
-------  ------  ----- -----    ----- -----    -----  -------
PF00685   1/1      24   292 ..     1   281 []  518.6  4.7e-152
```

FIGURE 2E

```
   1 AGTTCCAAAC TTTCCCACAT TTTCCTGTCT TCTTCTGTTC CAATCTCTGC
  51 CTGTTACCCA GTTCCAAAGT CAATTTTACA TTTTCAGGTA TCTGCAGTAG
 101 CACCCCACTC TGCTAGTACA AATTTATTGT ATTAGTCCCT TTTCATGCTG
 151 TTAATAAAGA CATACCTGAG ACTGGGCAAT TTAAAAAATA ACGAGGTTTA
 201 ACAGACTTAA AGTTCCACGT ATCTGGGGAA GCCTCACAGT CATGGTGGAA
 251 GGCAATGAAT GGCAGCAGGC AAAGGAAAAG AGAGCTTGTG CAGGGGAACT
 301 CCCCCTTATA ATGGGTGGGG ACACAGGCGA ACCATATCAG ACCCCAACTA
 351 AATTCCAAGT TTCCAGAGTT AGTAGACATG AGAGTTTTCA GGTACATGGG
 401 TACAAGAGAG TTTTTTCTGC TGTAACCCAT GACTGATATT TCAAAAATTA
 451 TTCCATGAAT GAAAAAAAAA CTACATGAAA TTATGTTTTT TGAAGATTTT
 501 CTCTGTGAAA ACTATTCAAG AAAATTGAGT ATAGAATGCT CCTTAAAACC
 551 ATTGTTTTGA ATTTTCTTCA ATGTAATTGT CTCGCTTCTA ATTATACAAA
 601 ATAATATCTT GAAGACAATG AAGCAATATA TGACACATAA CCCATTATAT
 651 TCCCGATTAA CAAGTAATAT GGTTGTTAGG TCATGCAGCA GGAAAAAGAC
 701 TATTTGGGTA TAAATCTCAG CCCCAACAGG TATTGATTAT TTTACTTTTA
 751 TCAAATTATT TAAACTTATA ATGACTTAAG TTTCCACATG TAGAAAACAG
 801 AAAAAACTAT TACCTATTTT ATGTGGTTGC TATGAAGATT AAATAATTAA
 851 TGTACATAGA GTAAGTTGTT AGCATGTTAT ATGTTAGCTT TCACTTATTT
 901 TATGCTATTC TAATCAAAGG CAGTAAGATG ATAACCCATA CTATGAACCA
 951 TAAAACAACA TTTTTAAAAA TTTTAATTAG TATTGATCTT ACCCATCCCA
1001 GATTCCCAAT GGCGAAGATT GAGAAAAACG CTCCCACGAT GGAAAAAAAG
1051 CCAGAACTGT TTAACATCAT GGAAGTAGAT GGAGTCCCTA CGTTGATATT
1101 ATCAAAAGAA TGGTGGGAAA AAGTATGTAA TTTCCAAGCC AAGCCTGATG
1151 ATCTTATTCT GGCAACTTAC CCAAAGTCAG GTAAGGGTAG CAAAACATAA
1201 AAATATTCAA TATTTTCACG TGAAATTATT GCATAATCTG TATTGATAAA
1251 TGAAGCATGA TTGGGATTTG GAGAGAAACA ATTCCTCATT ATGGAGATCT
1301 GTTCTTTGGT GCTGCAGGAC ATTTAGCATT CCTGATCCCT AGGACAACAA
1351 TTTCCAATAG CACTCTCTGA AGAGAACAGA AAAGATTTCT AAATGCTTTG
1401 GTAGTAGGGC AGATAATGCT CCCATTCCAG AACCCATAGC ATACATCAAA
1451 TATAAGGTCA ACAAATTGAA AGACCTATGG CTTTTTTAAA CATCAACCCT
1501 CAAGACAGCC TTCTAAAAGC ATGTCCTACT CCAAATATTA ATCTATTATC
1551 TCAGATATTA AACACAAATT GATTTTCTAA TCCTCTAAAG CTCTTGGAGG
1601 ATGTCAGCCA TGAATTTTCT GCTCTGTACC AAATTAGTCT CATTCAGAAA
1651 AGCCCAATGA CTGACCTTGA TTTAAAATGC CTTAGATTTC TAATTCTTCT
1701 CTAAAAATTC CTAGACTGGA ACACATGCTA GAGTCAATGG GCACACCTAA
1751 TGCCCAGAAC TCACTTTCGA TAGGCCATTC TCCATTAAAA TGAACCACAG
1801 CTATTAGGAG AATTGATGAT CCCACTCTTG GAATAGAAT ATGCAAGGGG
1851 AATGTACTAC ATCTTCTTTT TGAAGGAGTA AGTGATCAGT ATATATTCCC
1901 AGAATTGTTT GTTTGTATTA AATGTCTGTA AAAATAAAGC ACACATAATA
1951 ACAAAAAAAT TGATGGGGAC ATGTAGAAGG ATACAAGAAC CAACGTGAAG
2001 GGGCTCTCAC AGTAGCCACA TTTGGGACAG TTTGAGCATC CAAAAGAATG
2051 ATCACTAACT GATTGGGAGA ACATTAAATA AAAACCTCCT GGTCAGCCAT
2101 GCCGAAGGGA CAAGATTGGA TGTGTACTCC AGCCATAATA AAAAAGGAAA
2151 CTGGATAAAA TATATGAAAC CACTGGTTTC TGACCTTGGA TGACAGTTGT
2201 CTCAATCCTC AGACTGAAGA TGCTTTCTGA ATAGGGTATA GTTATAGGGT
2251 GCAAAAGAAA AAGCCATAGC AAACTCATTG AGTTCAAGAG CCAGGTGTAG
2301 GAGTTCTGAG AGGTTGAAGT GGCTGCTATT TGCAGGTAAG AGTACCAGAC
2351 AGAAGGAAAC TACACAAATA AATACCTTTA GATATCTTTA GAGAGGACCC
2401 TTTTAGTTTA TTGTTGAATG GTAGACTGCA CTTCCATAGA GCCTATAGCT
2451 CCATGAGATC AGGCAAGGAA CCACCAGAAA ACTATTAGCC ATATAATTCC
2501 TAGAGATTAT ACAAGCATGA GAGACTTTTG TGCTCCAATC AGGATAGGAT
2551 GGACAGAATT TTGGTCCCCA TGACATTAGT CCTCTGTTAT TACATCTGCC
2601 GTTATTTCAG ATTACATTCC CAAAAGGATT TTGCAGTTGC TATTAAACTA
2651 TCTAATCAGC TGATATTAAA ATAGGGAGAT TATTCTGGAC TATCTTGACG
2701 GACCCAGTGG AATCATGTGA ACAGGAAGTC AGAGAGATGT GGCAGAGGAG
2751 AAAGTCTGAG AAATTTAAAG TATAATAAAA GTTCACTGCA TGATTATAGA
2801 TTTAATGATG AAGAGAGAAA GTATCAACAA AACAGTTATC TCAATACTAC
2851 AGCCACAAGC AACTGAATTC TGTTGGCATC TAGGAGCTTG GCAAAACACC
2901 CTGAAGTCCC AGATGAGAAT GGCAGCCCTA GCTGATACCT TGATTTTAGC
```

FIGURE 3A

```
2951  CTAGTGAGAC CCTAAACAGA GGACTAGCCA TGTTAACCCC AATTTCTAAT
3001  CTACAGAAAC TATGACCGAA TATTCAGGTG TTGTTTTAAC TCATGAAGCT
3051  TGTGGTAATT TGTTAACCAC AAAGTCTTCA ACCTAGAATT CCATATACCC
3101  AGTAAAAATA ATATATTAAA ATATTACTAA AAATAAAGGT CAAAGACTTT
3151  TTCTCTGACA GCGAAAAGCT GAATGTGTTG CCCGCACAGC TGCACTAAAA
3201  ATAAATAAAT AAAAAGTTAT ATTAAAGAAA TTTATTCAGA GTAACAGAAA
3251  ATAATAGTAT ACAAAACTTT ATTATCTTTC AACATTCCAG CAACACACAG
3301  TTGGAATATG ACATTTTAAA AATACCATTG ATAAAATAAA TAGCACCTGA
3351  AAACATGAAA TATTCAGAAA TGAACTTAAC AAAGCTGTGC ATGATTTGAA
3401  AGTGAAAACA CTACGGAGAG AAATTGTATA AGACTTAAAT AAATAAGGAG
3451  GCATACCCTA TCTACGGATC AAAAGGATCA ATATTTTTAA GATATCAACT
3501  GTTTCAAAAT TAATGTATAA ATTCAATCTC AATCACAAAC TGACAAATTG
3551  ATTCCAAGAT TTCTATGAAA ATGTCATTAA AAGCAAATAT TTTTGATAGA
3601  GTAAAGTGGC AGGGTTTATA TTAACTGATT TCATGACATT TAACTCAGCT
3651  TCAACATTCA AAAGACTGTG ATACTGTTGA TATTGTTGAT AGACATAAAT
3701  ACTTGACCCT TACTTGGTGC CAGATGCAAA AAAGTCAAAG TGCAATGCAT
3751  CAGACCTCAA AAAATTAAAA TTAAATCTCT AAAACTATGG AAGTATAGAT
3801  AGGAGAATAG CTTCAAACTT TAGGTTAGGC AACAATAATT TGGGGAAAAA
3851  AATGGAAAGC ACTACCCTTT ATGGTTTGCA TTTAATGTAA ATTCAATATA
3901  AATTAGACTT AATCAAATTA AAACTTCTGT TCTTCTAAAG ACCCAGTTAA
3951  GAAAATAAAA ATATGTGACA TAGATGGAGA GAAAATATTC ACAATACATA
4001  TATCTGGCCA GAAGGTATAA AGAACTGTTA CAACTAAGAA CAAAAAACAA
4051  AAAAAAAATG TATTAAAGTG GGCAAAAGAT GTAAAAATGT ATCACCAAAA
4101  AAGCTTTACT ATTAACCAAT AAACACAAGA TATTCAACAT CATTTATCAT
4151  GAGAAAATGT AAATTAGTAC TATAATGAAA TACCACTACA CACCACTTCA
4201  AATGGCTAAA AACCTGGAAA TACTAAGTGT TGATAAGGAC ACAGAGCAAC
4251  TGAAATTCTC ATGAACTTTT GGGGAGGACC TAACATGGTA CTAATGTTGA
4301  ACAGTTTGTT ATAAAACTAA ACATGCACCT ACCACACAAC CCAGCAACTC
4351  CAATCCTAGA GATTCACCCC CACCCCCAAA ATAGAAATCT ATGTTCATAT
4401  AAAAACTTGT ACACAACACT ATAGCAGACT TATTCAAAAT TAGCCCAACA
4451  CTGAAGAAAA CCTAAATTCG TATTGTCATA TAAATGAATA AACAAATCAC
4501  TGCTTATCCA TACAATTGAA CTGTTCTCAG CAATTAAAAA AAATGAACTA
4551  CAGATATATA CAAGAACATA AATGAATCCC AAAATAATGA GGGTGTGTGA
4601  AAAAATTCAG ACACATGAGG ACAAACTGTA TGGTTTCATT TATATGAAAT
4651  TCAACAATGT GTAAAACTAA TTTGTATTGA CAAAAACATA GATCAGCAGT
4701  TCCGTGGAGT CGGAAGTGAG GAAAAGAATT ACTGATAGCA ACAGACACAA
4751  CGTTCTACTC TTATCTATGG TAATGGCTAC ATACATTTGT CAAATTTCCT
4801  TAAACTACAC ATTTATAACA GGTTCATTCT ATTCTATGTA ATTTTTACCA
4851  CACTGAAGTT TATTTCAAAA AACGTGATTC CATAATGATG AAAAATACAA
4901  AAAGAAAAAC TTATGTATTA TGATTGAAGA TAACTGTTAT TCATCTCTTA
4951  GACTAAAAAG AAGTAATTAA GAGAAAGAAT TTAGAGGAAT TGCAGTTCTT
5001  CCCTGATTTA TGAGGGAAAG TTCTTTATAT GAAGATCTAC CTAATAAATA
5051  GAGAAGTGAG GGGATTAGAA AATAAGCAAT TTGAAACCCA CAATAAAAAT
5101  TAGGTAAAGT AGGATCATTA ATGAATGAAT CTTAAAATAA TTAGATAAAA
5151  TATGAGGAGA ACTGGCTGGT CACATGGTAC TGAAATGTCA CCACATAGTT
5201  TTATTCCTAA AAGCAAATGG AAATATGGGC CTTTACAATG AGCGACCTGG
5251  TGGTCACCTA CAAAACTGAA TGATGAACAG TAGTATCACT AGTAGTGAGG
5301  CAATCAGACG TATGTACTTC TTGGCATGGT GCAAGAAGTA CCAAGCACTG
5351  CCTGAGAAAT CTGCCAAAAA TGTTCGCTAG AACCTAATCA AGACCTGGAT
5401  TCCAGTTTAT GGGAAATAGA GGAAATAGAG GAACAAAAAT GTACTGTGAA
5451  GAAATAATCA GACAAATCCA GAATGTGGGG AGTACTATAG GACAGCTGGC
5501  TAATTCGTTC AAAAACCAAT GTCAAGAAC AAAAATCAGT ATCATTAAGA
5551  AAAAATATGG AAAGATGATT CTAAGCTGAG ACAAAAAGGA TAGCAAAAGT
5601  AATGCAGCCA ATACATCTTA ATTGGGCAAA AGTGATTAAT AACATTATGA
5651  TACAATGGAA AAAAATTAAC ATAGGTTGAG TATCTCATGT TATTAAGGAT
5701  TTATTATAAA CTAGATGTGA TGAGAAACAT TTAGTAACCA TGATAAGAGA
5751  ATGTCATATT GGAAGATACA GCATTTTTGG CATGAAGTGT CATAATATAG
5801  GAAATGTAGA AATGGTTCAC TCAAACATGA TAGTTGAGAG ATTAAATACT
5851  AAAAGATGAT AGATAGATAG ACAGATAATA GGAAGATAGT AGATACATAC
```

FIGURE 3B

```
5901  ATACATACAT ACTTAGATAC ATAGATAGAT ACATAGATAC ATAAAGAAAC
5951  AGATGATAGA TTAGATAGAT AGATAGATAG ATAGATAGAT AGATAGATAG
6001  ATGGATAGAT AGATGGATAG ATAGATGCAG GTATAATACA ACAGTTTTCA
6051  TTTCTGCCTT GGCAACATTG ATCTAATTTT AAAGTGCTCT CATGTTGCTG
6101  TCTTTCTTCA AAATATTCAA TAACTTAGAA TGAAAGTTCA ATTGACTAAA
6151  ATTAAAGAAC TATTTCAAAT ATTTTCAGGT ACAACATGGA TGCATGAAAT
6201  TTTAGACATG ATTCTAAATG ATGGTGATGT GGAGAAATGC AAAAGAGCCC
6251  AGACTCTAGA TAGACACGCT TTCCTTGAAC TGAAATTTCC CCATAAAGAA
6301  AAACCAGGTG AGTAATATGC ACGAAGATAG AAAGGACTTT CACTTCAGGA
6351  TTCCAGAGCA ATGTGTACTG TCTCTGATAG AGCATCCGTG GTAGCCAGAA
6401  GTAGCCTGTA TCTTTCATGA GGTCTATTTG TTCTCAGGCC AACAATCAAA
6451  CTCTAGATTG GGTCTTCAGG GCTTCCTCCT GTTCTTAGCT GGTGGCCTTT
6501  ATCTCCCCAA TAAGATTTTC ATTCTCTTTC TCATATTTCT CCTACCCAAT
6551  GTTACGATAA AGAAGACTCC CTCTGCTTTG TATTCTCCTT CATATGTTTG
6601  AATCAGTGGA AAGGCCAGAA ATTAGCAATC AGCTATTGTA AAATAACAGG
6651  TGTGATTTCT GAAGAAAAAG GAGGAGAAGT AGGGGGGATA TACCGTGGAC
6701  ATTCCCAGAA TTAATTGGGG GAGCTGAAAA GGTTTCCTCA GAGTGTAAAA
6751  CCCAGTGAAT AACATGAAAT AAAGACAGAC CTCCTAGAGG TCTTTCTTTC
6801  CAAGAATGAC AACCTATTGT AAAAAAATGG ATGTAATTTC TGACAAACAA
6851  AAGAGAGAGA GAAAAAGAGA AAGGAAAAAA ACAACCAGAT ATATAACAAA
6901  CATTCCCAGA ATTAATCGAG GGTGAAAAAG AGCTTTCCTG AAAGTCTAAA
6951  AGCTGAGAGA ATAAGAGGAA ATAAGCAAAA CTCTCCTAGA AGGTTAGGCA
7001  GGATTGGATG CTTTGTATGT CCTTGTGGAT AAAAAATTAC TATTTCCAAT
7051  GGATATAAAA CAAAATATAA TCACTCTACA GACAAAGATA TAAATGGAAT
7101  TCAAGTATTT TGGCAGAGTG CCAAGAATAA ACAAAGAATA TAAATTGTTT
7151  CTTGCTAGAT TTGGAGTTCG TTCTTGAAAT GTCCTCACCA CAACTGATAA
7201  AAACACATCT CCCTTCACAT CTGATTCCAC CATCTATCTG GAAAGAAAAC
7251  TGCAAGGTAT AAAGAGGGGG CTTTTCAAAC TTCTCTTAGC TTGGTGATAT
7301  AAACTATACA ACTGAAGATA TCTTTCAAAA TAATATACTT TGAAAAATAT
7351  TTTCAAAAAT ATAATTTGCT ATTTTTCTTA GATGAAGCAC TTAAAATCAA
7401  GGATTACATA AATTTGAAAT CTGCAAACAT CCATGTTTTC TAAAATTCAT
7451  TTTCCTCTAA TCCTATTTCA TGAAAAATTC TTGGTAAGAT TTTCCAAAAT
7501  TGAGTCTGTG TTGCTACAAA TCAGAGAGTG TATTGGGAGC TAGAATGGAG
7551  GGAAACACAT TTAAAAATAA AACCCTGTTG CTTTGCTCTG CCAAAGTACT
7601  AGAAGATATT CTCCTGGCCT CAGAAGCAGA GGTATAGAAT CTGCTCTTGT
7651  CAAGGCTTCC ACACCTCCAT AATCTACTCA ATAAACTAAG CTCAAACCTG
7701  TCCTCATTTT TATCCCCCTC ACCTCTATGT CTGATCTGTC ACAAAGTCCA
7751  GTTCATTCTT CCCATCCTTC TAATCTGTGC ACTACACTGC AACACTACCA
7801  CCTGTACCCA ACTCAGCTCA CTGCTCTCTT TTGCCTCCCA CTTTGTCAGC
7851  CTGCCTCTAG ACCTGCCCCC TCCAACCCCT CCTCCCTGTA ACCTCTACTC
7901  TTCCTAAAAC ACAATCTGAC TGAGGTATTT CCCCACTATA AACACTTCCA
7951  CAGGTGGACG AAGATGCCTC CATATCCTCT ATATGACTTC CATGCCCTTG
8001  ACAGTCTGCA CCCTGCTCCA TCTCCTCCCC AGGGTCTTCC CATACCTGAT
8051  CCTCACTACA GTCCTCCTGA AATCCTGCAG GTCCTTTCAC ACATGGAGCA
8101  TCCCCACACC TTCCACATGC TCTCATCTGA CTCAAGCATC TCCTCATCTT
8151  TACTTGCATA ATTCCTACTT GTTCTTCTGG TCTTTTCATA GAGGGCCCCT
8201  ACAGGAAGCT TCTGTGACCC CATGGCTGAG TGAGTTTCAT GTATCTATAT
8251  TGGGGTATCT GTGCATGTGT TTCCCCATCA TTTTGTTCAC CACATTGCAT
8301  TATAATTTTC TCTCTTCTTA CCTCACTGAT CAGACTGTGA GCTCCTGACA
8351  GGCAGGGACT TGATCGTGCC CAATTTGTCA AGGTAAACAG TGTCTGGCAC
8401  GTAGGAAGAG TTAACATCTC TGTTCTGCAT TTGTTGACTG AATGATACTG
8451  AATTTCCAAT CATCACATCA CCATGCCCCT CTGTCCTAAC CATGTGAGAT
8501  ATGTGTGTGT GTGTGTATAT ATATATGTAT GTATATATAT GTATATATGT
8551  ATGTATGCAT ACATATGTAT GTATATATGT ATGTATGCAT ATATATGTAT
8601  ATATGTATGT ATGCATATAT ATGTATATAT GTGTATATAT ACACATATAT
8651  ATGTGTGTAT ATATATAGCA AAATCACTCA AATCTTTGAG AACCATTGTC
8701  TGAAACATTC CTCATGTGAG TCTCATACAA ATATCAAGGA ACTAGCTCTG
8751  GACTCAGTGT CCCAATTTTT GTGACCAGGC ATGACCCACT CGTGTACTAA
8801  GCATGGATTA GTGGTAGTGC CTCCAATCCT CTGAAGGTCA TTTACTTCTT
```

FIGURE 3C

```
8851  CTGTTGAAGG ATAACACCTA TTCTCTCCTT ACCTAACTCT AATCCTAATA
8901  GGAGCCAAAT GAGATGGTAT GCACAAAAAT GTTTTCTCAC TCTCTAGTAT
8951  TTCCCCTGTT GTAGGAATCT GGAAAATTTC TCTCAACTCA TTGAGACACA
9001  GCTGAAACTC ACCATTTCAT GGCCCATTCC CTGAATGCCC AGGAATGCTT
9051  TGTCACTGGC TCCATGATTA CTCAGCATAT CACATCATAT TCCATGATTG
9101  ACAGTGCTGT CCTAATAATG TGTTCATCTT CCTGCATAAC CAGGAAGAGT
9151  GGTTCCTCAT AACCACTCTG AAGTGGGGCA CTCTCATTTG TCTTTGTGTT
9201  CTCCATGGGT ATGAGGGTTG CAGAGTCAAA AAGACTCCAT TTATTTAATG
9251  TTTTAATTCA TAACTAATGT ATCTAATGCT ATAAACTTAT AGGATATGGT
9301  TACCATTGTA TTGAAACACT CACTTGAGTA TTTCATGTCA GTCTATTTTT
9351  CTCTCCATGG CTTCCTTCCC TCTCCTTGAT TTCAGATTGT CTATGTGGCC
9401  AGAAATCCCA AGGATTGCCT GGTGTCCTAC TACCACTTTC ACAGGATGGC
9451  TTCCTTTATG CCTGATCCTC AGAACTTAGA GGAATTTTAT GAGAAATTCA
9501  TGTCCGGAAA AGGTGAGTTC AAACTGATCT TTTTGGTACC CTCTTTCAGG
9551  TGACTCTAAC AATAAGCACC TCTGTAAACT GGAGGAGAAA GTTACAAAAG
9601  GCCATCCTGA TTGAGGAGGT CCTATCTTGA TGATCTGGGA CTGGAGAAGC
9651  CAGGTAGAAG AGGTATTTTT CCAAAATTGA GTACAAATGT AAATTGAGGT
9701  CAACTGGGGT CATAAGTTTT GAGACAAAGG TAAAAAGCCC CAAATCCTTG
9751  ACTTGAGTTT CAAACAATCA ACTTCAAAAT AAGAAGAGGC AACATTTCCT
9801  ATGGAAAGAC CTGGCAGTGG GAAGGCATGA GATGATATCC TGCGGTTTCA
9851  TCTTGCAGTG TGATTGGATG CCAGACCAC CACGTATAGT TACAAAAGTC
9901  ATACACTGCA CAGCCACAGA CAGCCTTTCC CGTAGGTCAC AGTGCACAAT
9951  CTTAGACCTG TTCACCTGCA GGAACCTCAC ATTAGAATTA GCAGCCATGA
10001 CCCCTCATCC ATTTATTAAG ATCACACCTT CCAGAGAAGC AGTGAACACA
10051 TTAGGGCCAC ACTTTTCAAA ATAGCAATTG ACTAGATTTG ACCAGGTGTC
10101 AAATCAGATT GGCAAGGATC TCAAACCCTT CACAGAAGAA GAATATCTCA
10151 TGAAAACAAC AATCTCTAGA CAGAAGAAAG ATAAGATGGC TACATAAAGT
10201 GATTTAGGAT GTAAGGACCA TCTTTACATA TTTGTATGAG CATTAATGCA
10251 GAAACATGAT TATAGTATTT CATTATAACT GCAGTGAGCA GAACCTAGAC
10301 AAATGGATAA ACATTACATG GTGTCTCCAC CATTTCACTA ACGTCTCTCA
10351 AATAATTAGA ACTTCCATAA GTGAAATGGG TGAGTTGTGA TGCTGAGAGC
10401 TCCCAGTCCT TGAGCAACCT AACTATCCCT GAGCAAGTGT GTTAGGGACC
10451 TGAGCTTCAT TATAACCAGT CCTGACATAT TCATATTCAT ATTCTTTTGA
10501 GGAAAAAGAA AAATCAAAAT GAAGTGACTT CCACAACATG ACCTGAATAA
10551 AAACAGATAT CTGTGGAAAA GTCAATAAAT AATAATTTCC ATCAAGCATG
10601 TCTCTCCAGT GAATCAAGAG AGATAACCTC ATTAGAACAT TTTCTCTAGA
10651 AACATAAATT AAAAAGGACT GACAGATGGA AATAAGAAAA ATAGCAAATC
10701 TAGATAGGAC TCCAGGTGAA TAGATTTCCA ATATTTATGC AGAGAAGTTT
10751 TGAGAGCAGG AAAAGTAGGA GGAAGCAGAG GAAGACAGGA TCCAAGCTTC
10801 TTTTCTTATA TGATTTTTTC CAAGGCCTAC ATTTTGTTAC TGTTTTTTTG
10851 TGTCAACTTG GCTGGATTGT GACACCTACA TATTTAATCA AACAACAATC
10901 CTGTTGTTTC TGTGAAAGTG TCAATTGTGT AGTTGTGATT TACATCTATA
10951 ATCAGTTGAC TTTAAGAAAA GGAGATAATG TTAAATATTA ATAATATGGG
11001 TGGTCTTTAT GCAATCACCT GAAGGTCTTA AGAGAAAAAA AACTCAGGTT
11051 TCCAAAAGAA AGGATTCTGC CTCAAGGCTG TTATATCAAA TCTTGCCTGA
11101 TTTTCCAGCA TCCCCTACAG ATTTAAAACA TGCCAAGACC CACAACTGCA
11151 GGAGCCAATT CCTTTAAATA AACCATATAT ACATAATATA CATTATATAT
11201 GTACATTTAT CTATATGTAC ATATTACATA GCCATTGCCT AAAATAAATT
11251 ATATGTGTAC ACATTTATAT TATGCATATA TATAAAACAT GCACACACAT
11301 ACATATACAT GGATGAGTCC CCTTTATACT TGGTTTCCCT TTCTGCAGTT
11351 TTAGTCACCC ACAATCAACC CCAATCCAAA AATATTACAG TATTTCAAGA
11401 GAAAGAAGGA TAGAGAGAGG GAGATTACAT TCACATAGAT GTAAATATAT
11451 TAGAGAATAT TGTTATAGAA GCTCTGTTTT ATTATTAGTT TTGTTGTAAT
11501 TCACTCACAG TGCCTAATAT AAAAATTAAA GTAATATACA CATCTATGTA
11551 TAGGAAAAAA CATAAACACT ATTATCATAT AATTTGGTAC TATCTGTGGT
11601 TTCAGGCATC CGCTGGGGGT CATGTGATAT ATCCCCTGTG CATAAGGATG
11651 AACTAATGTA TTCTTTGGAT TTGCCTATTG CTCTGTGTCT CTGGAGAACC
11701 TGGCTGACAC AGATACCAGT CACCATGACA CATGCCAAAG TTCAAGTCAC
11751 TGCAAACTTA CATCTCTGTT TGTCCTGATT CAAAAGAGAG CATTTCACAC
```

FIGURE 3D

```
11801 ACTTGCTCAC TTGGTCTGTG GTCATTTTCC TCTGGAGAAT GTTTTCCATC
11851 ATCCTTCAGA CGAATCTTCA AGTCCACTTA GCACAATGCT TGCAACATAG
11901 CTCACCCTGA ATAAAGATAG CTCCTGTGTT TATAATGACT GCCCAGAACC
11951 AAACCAGGAA GCTGCCAGAA GTTACAACCT ATCAGGGACA CTAAAACATC
12001 CCTGGGATAA AATATGGTGC TGGCTAACTC AGGTGTCCAC TCATTCTCTT
12051 ACCAACTAGT GAAAAGAAAA TGCATCCCAT GTTTACCACG TAGACACAGC
12101 CTCAGCTGGA AATAGAAGTT CTCCTGGAGG GCACCCCTCT TTCTGCTGCT
12151 GCTGAGTCTC TTTTGGAAGA GGAACTTGCA AACTGCATAG TGCAGCTATA
12201 CAGGGAAAGC AGCAGGAGGA CCCTACCCAT TTATAGGATG GCCTGAATTA
12251 GTTGAGTCTG AAACTAAACA TGGTTTACCA GGAACAGGGG AAGAATTTTA
12301 TTGCCGAATG TTTTAAGACA TGTCACAAGA CATAGTCAAT GTGTGCAAAG
12351 TCACATATAA TAAATGTGTA CTATAAATCT CGGCTTTACA CCATATAGAC
12401 AAATTTTATT ACTAGAAAAT TATTTCCACT TCGTTAAGGA ACCAGAACGA
12451 TAGTTACAGA AGCTTATTTC AAAGGAGCAC TAATTTACTT TATAGCCTTG
12501 GGTTTTGTCC CAGTACTGGG AACTAACAGT GCTCTGACTT CTTCCAGTTG
12551 TTGGCGGGTC CTGGTTTGAC CATGTGAAAG GATGGTGGGC TGCAAAAGAC
12601 ATGCACCGGA TCCTCTACCT CTTCTACGAG GATATTAAAA AAGTAAGTGG
12651 CACTGAGACT TATAGGTCAG ACCCAGAAAC CCTCCTGACA ATGTTATTCT
12701 GTTAAAAAGC TGTGTCTTTA ATTGGCCAAG TTCTTCTTCT TTCCTCCCTC
12751 TTCACAATGC CTTTTTCTCC CATGATCAGA ATCCAAAACA TGAGATCCAC
12801 AAGGTGTTGG AATTCTTGGA GAAACTTGG TCAGGTGATG TTATAAACAA
12851 GATTGTCCAC CATACCTCAT TTGATGTAAT GAAGGATAAT CCCATGGCCA
12901 ACCATACTGC GGTACCTGCT CACATATTCA ATCACTCCAT CTCAAAATTT
12951 ATGAGGAAAG GTTGGTGGCA TTTCTTTTCC TTAACTGAAC TCTAAAAAAT
13001 TTTCTACCCT ATATGCTAAA ATAATTTTCA ACCTAATTTT CAGGCAGAAG
13051 TGACTCATTT CAGTTAAATT TTGAATCTCT GCTCCCTTCA CCCTGCCTGT
13101 TTGCAGACAG CCAATGTCAG TGGTTCTGAA ACTTGAGTCA CATTAGAACC
13151 CCTGCAGGCC TTGCTAAAGC TCTGATTGCT GGTCCCCACT CAGAGATACT
13201 GATTCCACAG ATCCAGCAGT AGCCCTCAAA TTTGCTTTTC TCTCAAGTAC
13251 TCAGGTGATG CTGATCGTCC TGGTCACTTT GATTACAATA CCCACCTCAA
13301 CCATGAACTT CCCTTTGAAG GCTTGTGCAT CCTCTGAGCA GCTTTGAACA
13351 CTCATCTTTA GTCTATCCCT GTAGTTCAAA ACCCTAGCTA AGCACTTAGT
13401 ACTTGGATTT GTAACTACTG ATATTCATGT CTGTCTCCAA AATAAGATGA
13451 TAGGCTGTCC TGAAGAGAGT GTAGTGTTCA GTTTTGTTCC ACTAGAACCT
13501 AGTATAGAGA CTCATACCTC AAAACAACTC AGTAATGGCC TGTTGTGTGA
13551 GTGTACAGAT GAATGAACAT TATTTCTGTC CTCAACAAGT TAACATTCTA
13601 GATACATGCA AAAATAGCTG CAAAAAGTTA TAAACAAGAA AGTAAAGTGG
13651 AAGCTATACT AGGAATTCCC TAATACCAGT TCTCCTGGCT GTATCAAAAT
13701 TACCTTTAAA AACAGTGACC CCATTCCAGA ACATTCCAAT TAACTAGTTG
13751 CAAGCTGGAA TCTAGAATTT GATATTATGG GCAAGCATTT CAGATTAATC
13801 CTCTTGTCAA AGGGTAGGAA ACCAGTAGAA ATAAAGTACT AGGATAACTT
13851 AGAGAAACAA TTCATTAGTA CAGCATTTGT TGGGCTGACA AGGTACAACA
13901 GTTTGCAGAA GATCCCTAGT ATCCAAATGT CATTTCCAGT GGATTTACTA
13951 TTTAATTTTA CCCAACAAGT AATATCTTCT ACAATGAGGT TACTGACATC
14001 TTGTAACGTC TTTCACTGTC CCTGGGAGAA TAAGATAGGC TGTCCCCCAG
14051 GAAGTCCATG ATGGTAACCA GCTGTAGACT TTGGGTTGGG TACACTAGAG
14101 CCAGGAGTGT ACCCTGGAGC AGAAGATTCA GCACAGTGGG GCACCTCAGT
14151 GGGGCCTGCA GCATTTGAGG AAGGAGTATA AGGATGCTGT GTGCCTTGTG
14201 GTAAGAAAGC CAAGTGGAGT GGAAATGAGG GACCATTCAT AGTGGAAAGA
14251 CCAGAGGGAG TGGGACTGAG GGACCCTCAC TCATGGGAAA ATCACGTGGG
14301 TAGGCCTAGG AACCATTCAC TATAGAAAGG TTAGGTGGAA TGGGTGCAGA
14351 GTCTGTCATG AACTTCTTTG ATGTCCTACA GGGATGCCTG GAGACTGGAA
14401 GAACCACTTT ACTGTGGCTT TGAATGAGAA CTTTGATAAG CATTATGAAA
14451 AGAAGATGGC AGGGTCCACA CTGAACTTCT GCCTGGAGAT CTGAGAGGAA
14501 CAACAACAAA CTAGGTGACA GAGACTATGC CAACTATTTC GCCTTTTATT
14551 CTGTTGAGCA AGGAACTGTG ACTGAATGTG GAGCTTATGA GCTTCAGTCC
14601 ATCTCCTATA GTGTGGCTAG TTTGCTATAA TATTAAAACA TGATTTAAAA
14651 TATCAACAAA CCAGTTACTC CAGTAAATAA AATAAGAGAA TTAGAGAGCA
14701 GAGTCCGCCT ACATGAGTTT TTTTGTTTGT TTGTTTTTTA AGTACAGGTA
```

FIGURE 3E

```
14751  TGTTTTATTG TGCATGACAG ACAGAGCAAA AACAAACAAT TGCATCATGG
14801  ATTCCCATGT GTGATCCCAA GTAGATTTCA CAAGAAAATT ATGCATAGGT
14851  ATTACAAGCC CCATTGTTAA GAGAGAATGT AACAGCTTGA AGTGTACATT
14901  CTATACTTTT ATGTATAAAT AATAACTTCC AAGAGAAAAG AGCTGATAAG
14951  TACATTTCAG AGTCACCATT TCTGTAATAG AATGATATAA AAATAAATTA
15001  CTACTGCAAA ATATCAATCA ATTGCAAAAT GATTACTGCT CTACTTTTGG
15051  CTTGTAACTA ATTTTCTCAA TCGAAAGAGT TTGAGTTGGA GAAATTAGTC
15101  AGTGAGTACT CCTGTAAAAA ATCTTCCCAC GATATAAATA AAATGCTTAA
15151  TGTATCTAAT CTATAAATTG AGATCTGGGA CAAATGCACC ATGACTATGC
15201  ATTGCCATTC TCTTAATAAC TATGCATTGC CATTCTCTTA ATAAAGAGTC
15251  TCTGTTGCAT CACTCTAACA ATAGGTATGA CCTCAGATTT AATATAAATT
15301  TAGTGCTTCA ACCATGCACC AGTGAAGACC TGGTTTTTTA TATGACCAAG
15351  TACAATTGTC TTATTAGAAG AGAAGGTCCT GAGGGGCCTT AGGGAGTAGG
15401  TGGATGCCAA CAGGGCTGAT GGCCTCAGAG ATGACAGCAT GTAACATGTA
15451  AGAAAGGGGG GAAATTTGGA AAGACTTAAA CTCAGAAATA AAATTAAAGA
15501  AGTGTAAAAA GGTATTCAAT TAACATCTTG AAAGGGAATC AGGAACAATA
15551  TACATAGCTC CCAGTACACA GAGCAAAGTA ACCTCCCTGT GGTTGTGATC
15601  ATTGTCTCTA CCTTATCGTA GTGACAAGGC AGTGCTATTG TTACGCCAGG
15651  CAAAGGGGAA ATGACATCCT ATTCTCTAGT CAACTGGATG GAAGACAAAC
15701  TCAAAGGTAA AAAATAGATG ATGAGATTTT AAGAAAAGAG AGCAGCTGGT
15751  CCCTAAGGCC TGCTGTAAGG AAGCAGAGAG GATGAAGATG GGGGCATTTG
15801  AACCAGCCCA GAGGGGACCC TGGGGTGAAA GTTCCCCATC AGGCATTACC
15851  CCACTGCCTA CATCCAGCCA GATAACCCAA CCACCTGAAT TACCATCCTC
15901  ATATTTAGTT GGTGATCCAG AGAAGAGATT TCCTCTAGTA TTCCCTAAAG
15951  GTATAGCAAG AAAAAAAGAG ATTCCTTGAT CACTCCTGCC TAGTCAATGC
16001  ACTGGAAGAC TGGTTCACAG GGCTACTGTG CTTTGTAATT GGAGACATGA
16051  GAATCCACAA TGATTAGAAA GCTCGGGCCC CAGGTACTGT CAGAGTCCAC
16101  AGTCTACCTC AGAGAGGAGG AGGCAGATTA AAGGAAAAGC AAATTTCATT
16151  TTCCTACTCA GAAATGATTT TCTACTAATT GAAAAGCAAT TGAATGCTGT
16201  CAATAAAGAC ATTTCCTGTA CTAACCTTGG ACTCAGAGTA TTGATGACCA
16251  ACTATACAAA GCTTATTTCT TCCATGCAAT GGATGATACC TGCCTGCCTT
16301  TGCAGGTATT AAGGGGGTATG ATGCTGAGAG TCCAGGTGTA GAAGATGGGA
16351  TCACGGGTTT TGGGCAAAGC ATTTTGGCTA TCTAATGTTA AGAACTGTAA
16401  GGTTTGAGAA TGCCTTGATG AAAGTTCGTA AAAGCTACAA ACAGAGTTGC
16451  TGGTCATTTC TACAAGGAGG CTGTGAACTG CTCTTCATCT TCTAGAGGCA
16501  TATTTTGGCT ATGGGCTACT AAGATTCAGA CAGGTGTAAG ATATAGTTTG
16551  CCCCATGCC  TCCCCTAGAA CTTTCCCCAA TGTGACTGTT CCTGGACTAA
16601  ACTGAGGGTC GGGCTGCTAT TTCCTGTGGC CCAATAACAA GATGCAGATG
16651  AACTGGGGAG GAAGAGAAGT TTTATTTCTG TAACTGGTTA CATTCAGAGG
16701  GCCTGGAAAT TATCACCAAA CCAACTCAAA ATGACAAAAT TTTTCAGAGC
16751  TTATCTACCT TCTAAGCTGT ATGTCTACAT GTAAGTGTGC ATGCCTTCTA
16801  AAGACATATG TGATTAATTT ATTTTAATTT ATAACTAAGA TCTGAGTCCT
16851  GAAGACCTTC CTCTGGTGCC TAATGAAGTT TGCTTAATTT AAATGGGTCT
16901  CCAGGTACTG GGTTGATCAC CCTTATCTTG TCTCCTGTTA AACTACTGAG
16951  GTTTGGGGAG TTCCTTCAGA CCTCCAATAA ACGTGTTTGT GGAGGCCTGG
17001  GGAGTTTCTT CAGAGCCCCA ATAAAACTTA TATAATCCTA ACTGGGTACT
17051  GTTAAGAACT CCTTTATTAT TTTGTCATGT TGTAAGGCCC AGGAAACGCC
17101  TAGGCAAAAC TCTGGATGGG CTTTTGTTAC ATTTCAGCCT TTGCATAAGG
17151  GCACTGGCTT TTTTTAATAT TTAACTTAAC CACTCACTGA ATACTGAAAC
17201  AGTTGTGATG GAGGCCTGCA TTAATGCAAC CTGCCTGCCA CAATCCCCAC
17251  TGTCAATTTG TGCATAATTC TTATCATGCT AGTATATTTA TTTATCATGA
17301  GAATTGTAGG GATATGGGGC ATTGTAATAT TTCTGGCTAC TTCCTGCTGA
17351  GTGAGTGTCA TTGTTATGGG ACACTGAATG CAGCATTGGT ATAGGGGAGG
17401  TCTATTTGTT CCCAGCAGCA CTCTTTGTTT CAGGGGCTTA GAGGCAGCAC
17451  CTGCTGAAAC ATTTAGTCTT CAGTTCACAG GGCTTTAAGA AAGCACAACT
17501  TAGGTTTCAG TGATTTCCAG TTAGGAAAAA TGGGGTAGTG CATGGGCTTT
17551  CATGCAGAAG AGCCTTCAGT GCAAGTCCAT GACAATGTTT GCAACTCAGT
17601  TTTATCCTCA AAAGCTCTAA CTACTTTTTC GGTATTCTAA ATCTGCTTTG
17651  CTTTAATTCA GTTTTCAAAA TATTCTTCTT CCTCAGGAAA TAGCACATGC
```

FIGURE 3F

```
17701 TTTATAGTTG AATGAATCTG TTGGCTCCTG GCACTTGTAA GCCAGATATC
17751 TTTATCTGCA AAATGGTATC ATATCTATCT CATGAGATCA TTGTAAAGAT
17801 TTACACTATC ATACTTGTAA AGTGTACATA GTTGTGTTCA AGAAATTTAG
17851 CTTCCTTCTC CCTCTTGCAC ACCTCAACCC CACATCATAA AGCAAAGTTT
17901 AATCCATATA AACACTGGTA GGATTAGTCC CACATATTGG GACAGTGGAC
17951 TGATTTCTGA ATTTCAAACC ATCGTGTCTG AGTGTCTGCA CAAATTCACT
18001 CTCATGACCC AGTGCATCAG CATCCTAGAA TTACAAAACT AGCATCTGAG
18051 ATGTCCTCAG AAATTTAATC AAAAGCTATA GCTTTCTCTC TTTCTGTATC
18101 TCTTTGATCA AAAAGATCCA AGAAATAAGG ATCTATGCTT CTGGGTCAAC
18151 TTGAGATTCC TTTTATTCCT CCTCTTAGTG ACCTTCTGTT AAGTTCATAG
18201 GTTCTTTTTG CCATCTGTTG TAGTCCAAAT ACTAGAGTTA GTTATACTAT
18251 GCTTCACCAC CAACATTGTT CCTCCTTCAC ACAGCCTTTC CTGTTCTCCC
18301 CCAGGAGATA TCATTGCTCC TTCCCACCAA ATCTCCTGGC ACTCTGTCTG
18351 TACGTAGGCA GCATGTACTT TCTCAGCCAG CCTTGTGATT GTTTGTGTTT
18401 ATGCTTAATT CCTTTCCTTC AAGGTAAGCC TCTTGAGGGC AGGGACAACC
18451 CTCATCTTTG TGTTGCTACA GTATCTGGGA CAGTACAGTG TCTGGCACTA
18501 GGAGTCACTT GAGAAATATT TTTAAAATGT GTTCAAATGA TCCTTTAACT
18551 CATTTCTCTC CAAATACTGT CCAAATGGAA CATCATCCCC AAGGGAAGAC
18601 CCAACATGAT TTGTTTGGTG TGACTGTTCC ACATACAGGA CCCAAAGCGG
18651 GAAATTGAGA AGATACTGAA GTTCCTGGAA AAAGACATAT CAGAGGAAAT
18701 TCTGAATAAA ATCATCTATC ACACCTCCTT TGATGTAATG AAGCAAAACC
18751 CAATGACCAA CTATACCACT TTGCCCACCA GCATTATGGA CCACTCCATC
18801 TCCCCTTTTA TGAGGAAAGG TAGATAAGCT TTGTAGTCTA AGATGTCAAA
18851 TGGAACTCTG TGGTCCCCAT GGTCTGCTTA GATTTTCCAG TAATGTTTCA
18901 TTCTCCATTA TTTATTCTTT CCAGCAGCAC CACTGTACAA CCTTTGAGAG
18951 GCAAGTTGCC TGTTTCTCCT CATTCTTGGT GGGGTCCTAA GGGTGCATGC
19001 TTACCTCTCC CTCTACTCCT GCAGCAATCA TTAAGATTTT GCCTTGTTTC
19051 AGGGATGCCT GGAGACTGGA AGAACTATTT TACTGTGGCC CAAAATGAAG
19101 AATTTGACAA GGACTACCAG AAGAAGATGG CAGGAAGCAC CCTAACCTTC
19151 CGCACAGAGA TCTGAGAGCA GTCAGGGAGT CTGTCCTGGA CTTTCTTACC
19201 AGATTTTTGC CATTTGAGCC TCATGATCAA GGACACTTAA AACAAAGACA
19251 CCCTTCCTCC AGTCTGGAGC TGTTACACAC TACCTGTAGA TGATAATACT
19301 TCATCAAAAT GTAACCAAAT CCTGGGTAGA GTTTTTAATT AAGATACATG
19351 ATCCCTCATT TAGACACCAA CCACATAACG TACTCCCCTG TCCTAAGGCA
19401 AAATAAAGGC AATTTAGTTC CATCACTAGT TTACAATAGT GAAATAAATA
19451 AAGAGATAAA TAAGAGTAGA ATTTCAATGT AAGAGAAAGT GAGCAAGAGA
19501 AGAATGAGGA TGATAAGTGG GCACTAAGGA TAATGTGTGG GGGAACTGGT
19551 TTTTATTTTT AAAGGTCAGG AATGAGAGGC AGAGGATAGT CCTACTCTTG
19601 AAGATATTAG ATTAGGAGGT GCAGGGGGTG GCATGAAGGA TGGAATGCTG
19651 TGAGCTGGGT CTGGCTCAGG TGGCTTCAAG CTGAAATGGT CCCAAAACCA
19701 AAGAGAAAGG CCACAGGAGA GCGATAAGGA ACACAAGATG AACAAGAAAC
19751 TCAGCCTACT TCTGTGGCCA ACACAAGGCT GGAAAGCAGA GAAAGATTTT
19801 ATCTTTCAGA TGGACTTCTG AGAGAGAGAG GAAGTCTTCA GTGAGCTCAA
19851 GGGAAAAATA AAATAAAATA TTTGGTAACT CATGGACGTT AAGAAAAGCT
19901 TAAATTTCAC ATCTCTGTGG AAAATCGTTT TTTATACTTT TTTTTAAAGG
19951 GCTCTTAGCA AAACTGTCAG CATTGCCAAG TTCTTCAGCT ACACTAATGA
20001 TTATGTTCTT TTCCTTCTTT TTGTTAAAAC CTGTACCAAG AAAATATCTG
20051 CCATCATTTT ATACAAGCTA TACAACGATC CATGTATCAT TATTCTTTTA
20101 ATGTCAGGAA GGTACATTTT GTGGGATAGG TGGTTAACTT ATCATTAAAC
20151 CATACAACAC AAAAA
```
(SEQ ID NO:7)

FEATURES:
Transcript #1:
Start           1009
exon            1009-1180
5'UTR           1001-1008
intron 1181-6178

FIGURE 3G exon        6179-6307
intron 6308-7158
exon        7159-7256
intron 7257-9385
exon        9386-9512
intron 9513-12547
exon        12548-12642
intron 12643-12779
exon        12880-12960
intron 12961-14381
3'UTR       14491-14514
exon        14382-14514
Stop        14491

Transcript #2:
Start       1009
exon        1009-1180
5'UTR       1001-1008
intron 1181-6178
exon        6179-6307
intron 6308-7158
exon        7159-7256
intron 7257-9385
exon        9386-9512
intron 9513-12547
exon        12548-12642
intron 12643-18638
exon        18639-18819
intron 18820-19052
exon        19053-19165
Stop        19163 cDNA:
exon        1011-1180
5'UTR       1001-1008
intron 1181-6178
Start       1009
exon        6179-6307
intron 6308-7158
exon        7159-7256
intron 7257-9385
exon        9386-9512
intron 9513-12547
exon        12548-12642
intron 12643-12779
exon        12880-12960
intron 12961-14381
exon        14382-14506
Stop        14491
3'UTR       14491-14506

FIGURE 3H

Map position:
H1552     #     SHGCNAME      CHROM# LOD_SCORE   DIST.(cRs)
          1     SHGC-1639     2      10.01       16

Variants/SNPs:
| Position | Major | Minor | Protein coding/non-coding | | | | |
|---|---|---|---|---|---|---|---|
| 1,008 | a | c | exon, outside orf | | | | |
| 6,094 | a | g | intron | | | | |
| 7,898 | t | c | intron | | | | |
| 10,018 | a | c | intron | | | | |
| 10,791 | a | t | intron | | | | |
| 12,451 | a | t | intron | | | | |
| 14,674 | t | c | intron | | | | |
| 14,860 | g | c | intron | | | | |
| 20,133 | a | g | intron | | | | |
| 1,025 | a | c | exon | 39 | V | V | Protein 3 |
| 12,602 | t | c | exon | 194 | M | T | Protein 3 |
| 12,829 | g | t | exon | 224 | W | L | Protein 3 |
| 14,420 | a | t | exon | 281 | L | M | Protein 3 |

Context of variation:
DNA
Position
1,008     ttagtattgatcttacccatcccagattccc[a/c]atggcgaagattgagaaaaa
          (SEQ ID NO: 11)
6,094     gcaacattgatctaattttaaagtgctctcat[a/g]ttgctgtctttcttcaaaatattc
          (SEQ ID NO: 12)
7,898     ccaacccctcctccctgtaacctcta[t/c]tcttcctaaaacacaatct (SEQ ID NO: 13)
10,018    agcagccatgaccnctcatccatttatt[a/c]agatcacaccttccagaaa (SEQ ID NO: 14)
10,791    aggaggaagcagaggaagacagga[a/t]ccaagcttcttttcttatatgattttttcc
          (SEQ ID NO:15)
12,451    ccacttcgttaaggaaccagaacga[a/t]agttacagaagcttatttcaaaggag (SEQ ID NO: 16)
14,674    tttaaaatatcaacaaaccagttactccag[t/c]aaataaaataagagaattagagagcagagtc
          (SEQ ID NO: 17)
14,860    aggtattacaagc[g/c]ccattgttaagagagaatgtaacagctt (SEQ ID NO; 18)
20,133    ttttgtgggataggtg[a/g]ttaacttatcattaaacca (SEQ ID NO: 19)
1,025     GGTGGGAAAAAGT[a/c]TGTAATTTCCAAG (SEQ ID NO: 20)
12,602    GTGGGCTGCAAAAGACA[t/c]GCACCGGATC (SEQ ID NO: 21)
12,829    GGAGAAAACTT[g/T]GTCAGGTGATGTT (SEQ ID NO: 22)
14,420    ACTTTACTGTGGCT[A/t]TGAAT (SEQ ID NO: 23)

FIGURE 3I

ISOLATED HUMAN DRUG-METABOLIZING PROTEINS, NUCLEIC ACID MOLECULES ENCODING HUMAN DRUG-METABOLIZING PROTEINS, AND USES THEREOF

FIELD OF THE INVENTION

The present invention is in the field of proteins that are related to the sulfotransferase drug-metabolizing enzyme subfamily, recombinant DNA molecules and protein production. The present invention specifically provides novel drug-metabolizing peptides and proteins and nucleic acid molecules encoding such protein molecules, for use in labeling reagents with tagged sulfer and for the development of human therapeutics and human therapeutic development.

BACKGROUND OF THE INVENTION

Drug-Metabolizing Proteins

Induction of drug-metabolizing enzymes ("DMEs") is a common biological response to xenobiotics, the mechanisms and consequences of which are important in academic, industrial, and regulatory areas of pharmacology and toxicology.

For most drugs, drug-metabolizing enzymes determine how long and how much of a drug remains in the body. Thus, developers of drugs recognize the importance of characterizing a drug candidate's interaction with these enzymes. For example, polymorphisms of the drug-metabolizing enzyme CYP2D6, a member of the cytochrome p450 ("CYP") superfamily, yield phenotypes of slow or ultra-rapid metabolizers of a wide spectrum of drugs including antidepressants, antipsychotics, beta-blockers, and antiarrhythmics. Such abnormal rates of drug metabolism can lead to drug ineffectiveness or to systemic accumulation and toxicity.

For pharmaceutical scientists developing a candidate drug, it is important know as early as possible in the design phase which enzymes metabolize the drug candidate and the speed with which they do it. Historically, the enzymes on a drug's metabolic pathway were determined through metabolism studies in animals, but this approach has now been largely supplanted by the use of human tissues or cloned drug-metabolizing enzymes to provide insights into the specific role of individual forms of these enzymes. Using these tools, the qualitative and quantitative fate of a drug candidate can be predicted prior to its first administration to humans. As a consequence, the selection and optimization of desirable characteristics of metabolism are possible early in the development process, thus avoiding unanticipated toxicity problems and associated costs subsequent to the drug's clinical investigation. Moreover, the effect of one drug on another's disposition can be inferred.

Known drug-metabolizing enzymes include the cytochrome p450 ("CYP") superfamily, N-acetyl transferases ("NAT"), UDP-glucuronosyl transferases ("UGT"), methyl transferases, alcohol dehydrogenase ("ADH"), aldehyde dehydrogenase ("ALDH"), dihydropyrimidine dehydrogenase ("DPD"), NADPH:quinone oxidoreductase ("NQO" or "DT diaphorase"), catechol O-methyltransferase ("COMT"), glutathione S-transferase ("GST"), histamine methyltransferase ("HMT"), sulfotransferases ("ST"), thiopurine methyltransferase ("TPMT"), and epoxide hydroxylase. Drug-metabolizing enzymes are generally classified into two phases according to their metabolic function. Phase I enzymes catalyze modification of functional groups, and phase II enzymes catalyze conjugation with endogenous substituents. These classifications should not be construed as exclusive nor exhaustive, as other mechanisms of drug metabolism have been discovered. For example, the use of active transport mechanisms been characterized as part of the process of detoxification.

Phase I reactions include catabolic processes such as deamination of aminases, hydrolysis of esters and amides, conjugation reactions with, for example, glycine or sulfate, oxidation by the cytochrome p450 oxidation/reduction enzyme system and degradation in the fatty acid pathway. Hydrolysis reactions occur mainly in the liver and plasma by a variety of non-specific hydrolases and esterases. Both deaminases and amidases, also localized in the liver and serum, carry out a large part of the catabolic process. Reduction reactions occur mainly intracellularly in the endoplasmic reticulum.

Phase II enzymes detoxify toxic substances by catalyzing their conjugation with water-soluble substances, thus increasing toxins' solubility in water and increasing their rate of excretion. Additionally, conjugation reduces the toxins' biological reactivity. Examples of phase II enzymes include glutathione S-transferases and UDP-glucuronosyl transferases, which catalyze conjugation to glutathione and glucuronic acid, respectively. Transferases perform conjugation reactions mainly in the kidneys and liver.

The liver is the primary site of elimination of most drugs, including psychoactive drugs, and contains a plurality of both phase I and phase II enzymes that oxidize or conjugate drugs, respectively.

Physicians currently prescribe drugs and their dosages based on a population average and fail to take genetic variability into account. The variability between individuals in drug metabolism is usually due to both genetic and environmental factors, in particular, how the drug-metabolizing enzymes are controlled. With certain enzymes, the genetic component predominates and variability is associated with variants of the normal, wild-type enzyme.

Most drug-metabolizing enzymes exhibit clinically relevant genetic polymorphisms. Essentially all of the major human enzymes responsible for modification of functional groups or conjugation with endogenous subsituents exhibit common polymorphisms at the genomic level. For example, polymorphisms expressing a non-functioning variant enzyme results in a sub-group of patients in the population who are more prone to the concentration-dependent effects of a drug. This sub-group of patients may show toxic side effects to a dose of drug that is otherwise without side effects in the general population. Recent development in genotyping allows identification of affected individuals. As a result, their atypical metabolism and likely response to a drug metabolized by the affected enzyme can be understood and predicted, thus permitting the physician to adjust the dose of drug they receive to achieve improved therapy.

A similar approach is also becoming important in identifying risk factors associated with the development of various cancers. This is because the enzymes involved in drug metabolism are also responsible for the activation and detoxification of chemical carcinogens. Specifically, the development of neoplasia is regulated by a balance between phase I enzymes, which activate carcinogens, and phase II enzymes, which detoxify them. Accordingly, an individual's susceptibility to cancer often involves the balance between these two processes, which is, in part, genetically determined and can be screened by suitable genotyping tests. Higher induction of phase I enzymes compared to phase II enzymes results in the generation of large amounts of electrophiles and reactive oxygen species and may cause DNA and membrane damage and other adverse effects leading to neoplasia. Conversely, higher levels of phase II enzyme expression can protect cells from various chemical compounds.

Abnormal activity of drug-metabolizing enzymes has been implicated in a range of human diseases, including cancer, Parkinson's disease, myetonic dystrophy, and developmental defects.

Cytochrome p450

An example of a phase I drug-metabolizing enzyme is the cytochrome p450 ("CYP") superfamily, the members of which comprise the major drug-metabolizing enzymes expressed in the liver. The CYP superfamily comprises heme proteins which catalyze the oxidation and dehydrogenation of a number of endogenous and exogenous lipophilic compounds. The CYP superfamily has immense diversity in its functions, with hundreds of isoforms in many species catalyzing many types of chemical reactions. The CYP superfamily comprises at least 30 related enzymes, which are divided into different families according to their amino acid homology. Examples of CYP families include CYP families 1, 2, 3 and 4, which comprise endoplasmic reticulum proteins responsible for the metabolism of drugs and other xenobiotics. Approximately 10–15 individual gene products within these four families metabolize thousands of structurally diverse compounds. It is estimated that collectively the enzymes in the CYP superfamily participate in the metabolism of greater than 80% of all available drugs used in humans. For example, the CYP1A subfamily comprises CYP1A2, which metabolizes several widely used drugs, including acetaminophen, amitriptyline, caffeine, clozapine, haloperidol, imipramine, olanzapine, ondansetron, phenacetin, propafenone, propranolol, tacrine, theophylline, verapamil. In addition, CYP enzymes play additional roles in the metabolism of some endogenous substrates including prostaglandins and steroids.

Some CYP enzymes exist in a polymorphic form, meaning that a small percentage of the population possesses mutant genes that alter the activity of the enzyme, usually by diminishing or abolishing activity. For example, a genetic polymorphism has been well characterized with the CYP2C19 and CYP2D6 genes. Substrates of CYP 2C19 include clomipramine, diazepam, imipramine, mephenytoin, moclobemide, omeprazole, phenytoin, propranolol, and tolbutamide. Substrates of CYP 2D6 include alprenolol, amitriptyline, chlorpheniramine, clomipramine, codeine, desipramine, dextrometlhorphan, encainide, fluoxetine, haloperidol, imipramine, indoramin, metoprolol, nortriptyline, ondansetron, oxycodone, paroxetine, propranolol, and propafenone. Polymorphic variants of these genes metabolize these substrates at different rates, which can effect a patient's effective therapeutic dosage.

While the substrate specificity of CYPs must be very broad to accommodate the metabolism of all of these compounds, each individual CYP gene product has a narrower substrate specificity defined by its binding and catalytic sites. Drug metabolism can thereby be regulated by changes in the amount or activity of specific CYP gene products. Methods of CYP regulation include genetic differences in the expression of CYP gene products (i.e., genetic polymorphisms), inhibition of CYP metabolism by other xenobiotics that also bind to the CYP, and induction of certain CYPs by the drug itself or other xenobiotics. Inhibition and induction of CYPs is one of the most common mechanisms of adverse drug interactions. For example, the CYP3A subfamily is involved in clinically significant drug interactions involving nonsedating antihistamines and cisapride that may result in cardiac dysrhythmias. In another example, CYP3A4 and CYP1A2 enzymes are involved in drug interactions involving theophylline. In yet another example, CYP2D6 is responsible for the metabolism of many psychotherapeutic agents. Additionally, CYP enzymes metabolize the protease inhibitors used to treat patients infected with the human immunodeficiency virus. By understanding the unique functions and characteristics of these enzymes, physicians may better anticipate and manage drug interactions and may predict or explain an individual's response to a particular therapeutic regimen.

Examples of reactions catalyzed by the CYP superfamily include peroxidative reactions utilizing peroxides as oxygen donors in hydroxylation reactions, as substrates for reductive beta-scission, and as peroxyhemiacetal intermediates in the cleavage of aldehydes to formate and alkenes. Lipid hydroperoxides undergo reductive beta-cleavage to give hydrocarbons and aldehydic acids. One of these products, trans-4-hydroxynonenal, inactivates CYP, particularly alcohol-inducible 2E1, in what may be a negative regulatory process. Although a CYP iron-oxene species is believed to be the oxygen donor in most hydroxylation reactions, an iron-peroxy species is apparently involved in the deformylation of many aldehydes with desaturation of the remaining structure, as in aromatization reactions.

Examples of drugs with oxidative metabolism associated with CYP enzymes include acetaminophen, alfentanil, alprazolam, alprenolol, amiodarone, amitriptyline, astemizole, buspirone caffeine, carbamazepine, chlorpheniramine, cisapride, clomipramine, clomipramine, clozapine, codeine, colchicine, cortisol, cyclophosphamide, cyclosporine, dapsone, desipramine, dextromethorphan, diazepam, diclofenac, diltiazem, encainide, erythromycin, estradiol, felodipine, fluoxetine, fluvastatin, haloperidol, ibuprofen, imipramine, indinavir, indomethacin, indoramin, irbesartan, lidocaine, losartan, macrolide antibiotics, mephenytoin, methadone, metoprolol, mexilitene, midazolam, moclobemide, naproxen, nefazodone, nicardipine, nifedipine, nitrendipine, nortriptyline, olanzapine, omeprazole, ondansetron, oxycodone, paclitaxel, paroxetine, phenacetin, phenytoin, piroxicam, progesterone, propafenone, propranolol, quinidine, ritonavir, saquinavir, sertraline, sildenafil, S-warfarin, tacrine, tamoxifen, tenoxicam, terfenadine, testosterone, theophylline, timolol, tolbutamide, triazolam, verapamil, and vinblastine.

Abnormal activity of phase I enzymes has been implicated in a range of human diseases. For example, enhanced CYP2D6 activity has been related to malignancies of the bladder, liver, pharynx, stomach and lungs, whereas decreased CYP2D activity has been linked to an increased risk of Parkinson's disease. Other syndromes and developmental defects associated with deficiencies in the CYP superfamily include cerebrotendinous xanthomatosis, adrenal hyperplasia, gynecomastia, and myetonic dystrophy.

The CYP superfamily are a major target for drug action and development. Accordingly, it is valuable to the field of pharmaceutical development to identify and characterize previously unknown members of the CYP superfamily.

UDP-Glucuronosyltransferases

Potential drug interactions involving phase II metabolism are increasingly being recognized. An important group of phase II enzymes involved in drug metabolism are the glucuronosyltransferases, especially the UDP-glucuronyltransferase ("UGT") superfamily. Members of the UGT superfamily catalyze the enzymatic addition of UDP glucuronic acid as a sugar donor to fat-soluble chemicals, a process which increases their solubility in water and increases their rate of excretion. In mammals, glucuronic acid is the main sugar that is used to prevent the accumulation of waste products of metabolism and fat-soluble chemicals from the environment to toxic levels in the body. Both inducers and inhibitors of glucuronosyltransferases are known and have the potential to affect the plasma concentration and actions of important drugs, including psychotropic drugs.

The UGT superfamily comprises several families of enzymes in several species defined with a nomenclature similar to that used to define members of the CYP superfamily. In animals, yeast, plants and bacteria there are at least 110 distinct known members of the UGT superfamily. As many as 33 families have been defined, with three families identified in humans. Different UGT families are defined as having <45% amino acid sequence homology; within subfamilies there is approximately 60% homology. The members of the UGT superfamily are part of a further superfamily of UDP glycosyltransferases found in animals, plants and bacteria.

The role of phase II enzymes, and of UGT enzymes in particular, is being increasingly recognized as important in psychopharmacology. UGT enzymes conjugate many important psychotropic drugs and are an important source of variability in drug response and drug interactions. For example, the benzodiazepines lorazepam, oxazepam, and temazepam undergo phase II reactions exclusively before being excreted into the urine.

Phase II enzymes metabolize and detoxify hazardous substances, such as carcinogens. The expression of genes encoding phase II enzymes is known to be up-regulated by hundreds of agents. For example, oltipraz is known to up-regulate phase II enzyme expression. Studies have demonstrated protection from the cancer-causing effects of carcinogens when selected phase II enzyme inducers are administered prior to the carcinogens. The potential use of phase II enzyme inducers in humans for prevention of cancers related to exposure to carcinogens has prompted studies aimed at understanding their molecular effects. Current biochemical and molecular biological research methodologies can be used to identify and characterize selective phase IT enzyme inducers and their targets. Identification of genes responding to cancer chemopreventive agents will facilitate studies of their basic mechanism and provide insights about the relationship between gene regulation, enzyme polymorphism, and carcinogen detoxification.

Examples of drugs with conjugative metabolism associated with UGT enzymes include amitriptyline, buprenorphine, chlorpromazine, clozapine, codeine, cyproheptadine, dihydrocodeine, doxepin, imipramine, lamotrigine, lorazepam, morphine, nalorphine, naltrexone, temazepam, and valproate.

Abnormal activity of phase II enzymes has been implicated in a range of human diseases. For example, Gilbert syndrome is an autosomal dominant disorder caused by mutation in the UGT1 gene, and mutations in the UGT1A1 enzyme have been demonstrated to be responsible for Crigler-Najjar syndrome.

The UGT superfamily are a major target for drug action and development. Accordingly, it is valuable to the field of pharmaceutical development to identify and characterize previously unknown members of the UGT superfamily.

Sulfotransferases

Sulfation and sulfate conjugate hydrolysis play an important role in metabolism, and are catalysed by members of the sulfotransferase and sulfatase enzyme superfamilies. Sulfotransferases are enzymes that transfer sulfate groups to acceptor molecules. These enzymes are involved in the posttranslational sulfation of proteins and the sulfate conjugation of exogenous chemicals and bile acids. Cytosolic sulfotransferases in mammalian cells catalyze the transfer of a sulfonate group from 3'-phosphoadenosine-5'-phosphosulfate, the active sulfate, to the hydroxyl groups or amine groups of substrate compounds. Traditionally, they are viewed as detoxifying or Phase II drug-metabolizing enzymes that facilitate the removal of drugs and xenobiotic compounds. Increasingly, however, these enzymes have been shown to be involved in the sulfation of endogenous compounds, such as thyroid and steroid hormones, catecholamines, and bile acids, to fulfill fundamental biochemical/physiological needs. The balance of sulfoconjugation (by sulfotransferases) and deconjugation (by sulfotases) may have physiological implications; in addition to catecholamine release, it may determine the availability of free catecholamines during diurnal rhythms and stress or modify their renal excretion. Circumstantial evidence, including a close homology within the aryl sulfatases and steroid sulfatase gene, the first implicated in catecholamine metabolism, the second in steroid metabolism, suggests a genetic defect of sulfatases in essential hypertension. A similar, but secondary, sulfatase defect may affect catecholamine metabolism and action in chronic renal failure.

In general, sulfation is a deactivating, detoxication pathway, but for some chemicals the sulfate conjugates are much more reactive than the parent compound (Coughtrie M W, et al., 1998. Biology and function of the reversible sulfation pathway catalysed by human sulfotransferases and sulfatases. Chem Biol Interact. 20;109(1–3):3–27). For example N-hydroxyarylamine sulfotransferase (HAST-I) detoxifies phenols but activates N-hydroxylarylamines into a mutagenic form, N-hydroxy-2-acetylaminofluorene (Nagata, K., et al., 1993. Isolation and expression of a cDNA encoding a male-specific rat sulfotransferase that catalyzes activation of N-hydroxy-2-acetylaminofluorene. J. Biol. Chem. 268 (33), 24720–24725 and Gong D W, et al., 1991. Purification of hepatic N-hydroxyarylamine sulfotransferases and their regulation by growth hormone and thyroid hormone in rats. *J Biochem* (Tokyo) 1991 August; 110(2): 226–31.).

The discovery of proteins that are related to and are potentially new sulfotransferase satisfies a need in the art by providing new compositions which are useful towards the design of stable and more active drugs, and in the prevention, diagnosis, and treatment of cancer, hypertension, renal diseases, and neurodegenerative diseases.

In addition to such use in the study of drug metabolism, sulfotransferases are also useful in labeling agents with tagged sulfur. This provides another use of the proteins of the present invention.

Further, since the genes of the present invention are mapped to chromosomal position and SNP variation is present, the nucleic acid molecules of the present invention can be used in linkage studies and genetic mapping uses.

SUMMARY OF THE INVENTION

The present invention is based in part on the identification of amino acid sequences of proteins that are related to the sulfotransferase drug-metabolizing enzyme subfamily, as well as allelic variants and other mammalian orthologs thereof. These unique protein sequences, and nucleic acid sequences that encode these proteins, can be used to label proteins, as models for the development of human therapeutic targets, aid in the identification of therapeutic proteins, and serve as targets for the development of human therapeutic agents that modulate protein of the present invention activity in cells and tissues that express the protein of the present invention. Specifically, experimental data provided in FIG. 1 shows that the sulfotransferase of the present invention is expressed at least in the kidney and small intestine. Further, the nucleic acid molecules herein described can be used to label agents with tagge sulfur.

DESCRIPTION OF THE FIGURE SHEETS

FIG. 1 provides the nucleotide sequence of two alternative transcript sequences (SEQ ID NOS:1 and 2) and a cDNA sequence (SEQ ID NO:3) that encodes the protein of the present invention. In addition, structure and functional information is provided, such as ATG start, stop and tissue distribution, that allows one to readily determine specific uses of inventions based on this molecular sequence. Experimental data provided in FIG. 1 shows that the sulfotransferase of the present invention is expressed at least in the kidney and small intestine.

FIG. 2 provides the amino acid sequences of the proteins of the present invention. (SEQ ID NOS:4–6) In addition, structural and functional information such as protein family, function, important domains and modification sites is provided, allowing one to readily determine specific uses of inventions based on this molecular sequence.

FIG. 3 provides genomic sequences that span the gene encoding the protein of the present invention. (SEQ ID NO:7) In addition structural and functional information, such as intron/exon structure, promoter location, etc., is provided allowing one to readily determine specific uses of inventions based on this molecular sequence. For example, as illustrated in FIG. 3, identified SNP variations include a1008c, a6094g, t7898c, a10018c, a10791t, a12451t, t14674c, g14860c, a20133g, a1025c, t12602c, g12829t, a1442t.

DETAILED DESCRIPTION OF THE INVENTION

General Description

The present invention is based on the gene identification that occurred during the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a drug-metabolizing enzyme protein or part of a drug-metabolizing enzyme protein and are specifically related to the sulfotransferase drug-metabolizing enzyme subfamily. Utilizing these sequences, additional genomic sequences were assembled and transcript and/or cDNA sequences were isolated and characterized. Based on this analysis, the present invention provides amino acid sequences of proteins that are related to the sulfotransferase drug-metabolizing enzyme subfamily, nucleic acid sequences in the form of transcript sequences, cDNA sequences and/or genomic sequences that encode these proteins, nucleic acid variation (allelic information), tissue distribution of expression, and information about the closest art known protein/peptide/domain that has structural or sequence homology to the protein of the present invention.

In addition to being previously unknown, the proteins that are provided in the present invention are selected based on their ability to be used for the development of commercially important products and services. Specifically, the present proteins are selected based on homology and/or structural relatedness to known drug-metabolizing enzyme proteins of the sulfotransferase drug-metabolizing enzyme subfamily and the expression pattern observed. Specifically, experimental data provided in FIG. 1 shows that the sulfotransferase of the present invention is expressed at least in the kidney and small intestine. The art has clearly established the commercial importance of members of this family of proteins and proteins that have expression patterns similar to that of the present gene for industrial uses, such as labeling agents with tagged sulfur, genetic mapping uses, use of the SNP and chromosomal position for linkage studies, genetic expression uses, use of the control region to drive expression in the kidneys, etc. Some of the more specific features of the proteins of the present invention, and the uses thereof, are described herein, particularly in the Background of the Invention and in the annotation provided in the Figures, and/or are known within the art for the known sulfotransferase subfamily of drug-metabolizing enzyme proteins.

Specific Embodiments

Peptide Molecules

The present invention provides nucleic acid sequences that encode protein molecules that have been identified as being related to the sulfotransferase drug-metabolizing enzyme subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the proteins of the present invention, or proteins of the present invention.

The present invention provides isolated peptide and protein molecules that consist of, consist essentially of, or comprise the amino acid sequences of the proteins disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The proteins of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the peptide having less than about 30% (by dry weight) chemical precursors or other chemicals, less than about 20% chemical precursors or other chemicals, less than about 10% clinical precursors or other chemicals, or less than about 5% chemical precursors or other chemicals.

The isolated protein can be purified from cells that naturally express it, purified from cells that have been altered to express it (recombinant), or synthesized using known protein synthesis methods. Experimental data provided in FIG. 1 shows that the sulfotransferase of the present invention is expressed at least in the kidney and small intestine. For example, a nucleic acid molecule encoding the proteins of the present invention is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NOS:4–6), for example, proteins encoded by the transcript/cDNA nucleic acid sequences shown in FIG. 1 (SEQ ID NOS :1 and 2, alternative transcript sequences, and SEQ ID NO:3, cDNA sequences) and the genomic sequences provided in FIG. 3 (SEQ ID NO:7). The amino acid sequence of such a protein is provided in FIG. 2. A protein consists of an amino acid sequence when the amino acid sequence is the final amino acid sequence of the protein. Such a protein can further comprise the variants provided in FIG. 3.

The present invention further provides proteins that consist essentially of the amino acid sequences provided in FIG. 2 (SEQ ID NOS:4–6), for example, proteins encoded by the transcript/cDNA nucleic acid sequences shown in FIG. 1 (SEQ ID NOS:1 and 2, alternative transcript sequences, and SEQ ID NO:3, cDNA sequences) and the genomic sequences provided in FIG. 3 (SEQ ID NO:7). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NOS:4–6), for example, proteins encoded by the transcript/cDNA nucleic acid sequences shown in FIG. 1 (SEQ ID NOS:1 and 2, alternative transcript sequences, and SEQ ID NO:3, cDNA sequences) and the genomic sequences provided in FIG. 3 (SEQ ID NO:7). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the proteins of the present invention are the naturally occurring mature proteins. A brief description of how various types of these proteins can be made/isolated is provided below.

The proteins of the present invention can be attached to heterologous sequences to form chimeric or fusion proteins. Such chimeric and fusion proteins comprise one of the proteins of the present invention operatively linked to a heterologous protein having an amino acid sequence not substantially homologous to the proteins of the present invention. "Operatively linked" indicates that the proteins of the present invention and the heterologous protein are fused in-frame. The heterologous protein can be fused to the N-terminus or C-terminus of the proteins of the present invention.

In some uses, the fusion protein does not affect the activity of the proteins of the present invention per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant proteins of the present invention. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et cl., *Current Protocols in Molecular Biology*, 1992). Moreover, many expression vectors are commercially available that already encode a fusion moiety (e.g., a GST protein). A protein of the present invention-encoding nucleic acid can be cloned into such an expression vector such that the fusion moiety is linked in-frame to the proteins of the present invention.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the proteins of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, and splice variants proteins that comprise one of the proteins of the present invention can readily be identified as having complete sequence identity to at least a portion of one of the proteins of the present invention as well as being encoded by the same genetic locus as the proteins of the present invention provided herein. FIG. 3, the map position was determined to be on chromosome 2 near marker SHGC-1639 (LOD score 10.01) using radiation hybrid mapping.

Allelic variants of a protein of the present invention can readily be identified as being a human protein having a high degree (significant) of sequence homology/identity to at least a portion of the proteins of the present invention as well as being encoded by the same genetic locus as the proteins of the present invention provided herein. Genetic locus can readily be determined based on the genomic information provided in FIG. 3, such as the genomic sequence mapped to the reference human. As indicated by the data presented in FIG. 3, the map position was determined to be on chromosome 2 near marker SHGC-1639 (LOD score 10.01) using radiation hybrid mapping. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a protein of the present invention encoding nucleic acid molecule under stringent conditions as more fully described below.

FIG. 3 provides SNP information that was identified from chromosomal sequence obtained from a number of individuals as well as SNPs found during the cDNA cloning process. These include, a6094g, t7898c, a10018c, a10791t, a12451t, t14674c, g14860c, a20133g, a1025c, t12602c, g12829t, a1442t.

Paralogs of a protein of the present invention can readily be identified as having some degree of significant sequence homology/identity to at least a portion of the proteins of the present invention, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a protein of the present invention encoding nucleic acid molecule under moderate to stringent conditions as more fully described below.

Orthologs of a protein of the present invention can readily be identified as having some degree of significant sequence homology/identity to at least a portion of the proteins of the present invention as well as being encoded by a gene from another organism. Preferred orthologs will be isolated from mammals, preferably primates, for the development of human therapeutic targets and agents. Such orthologs will be encoded by a nucleic acid sequence that will hybridize to a protein of the present invention encoding nucleic acid molecule under moderate to stringent conditions, as more fully described below, depending on the degree of relatedness of the two organisms yielding the proteins.

Non-naturally occurring variants of the proteins of the present invention can readily be generated using recombinant techniques. Such variants include, but are not limited to deletions, additions and substitutions in the amino acid sequence of the proteins of the present invention. For example, one class of substitutions are conserved amino acid substitution. Such substitutions are those that substitute a given amino acid in a protein of the present invention by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant proteins can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as drug-metabolizing enzyme activity or in assays such as an in vitro proliferative activity. Sites that are critical for binding partner/substrate binding can also be determined by structural analysis such as crystallization, nuclear magnetic resonance or photoaffinity labeling (Smith et al, *J. Mol. Biol.* 224:899–904 (1992); de Vos et al. *Science* 255:306–312 (1992)).

The present invention further provides fragments of the proteins of the present invention, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a protein of the present invention. Such fragments can be chosen based on the ability to retain one or more of the biological activities of the proteins of the present invention or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the proteins of the present invention, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in proteins are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylatioon, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins,* B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the proteins of the present invention also encompass derivatives or analogs in which a substituted amino acid residue is not one encoded by the genetic code, in which a substituent group is included, in which the mature protein of the present invention is fused with another compound, such as a compound to increase the half-life of the protein of the present invention (for example, polyethylene glycol), or in which the additional amino acids are fused to the mature protein of the present invention, such as a leader or secretory sequence or a sequence for purification of the mature protein of the present invention or a pro-protein sequence.

Protein/Peptide Uses

The proteins of the present invention can be used in substantial and specific assays related to the functional information provided in the Figures; to label agents with tagged sulfur, to raise antibodies or to elicit another immune response; as a reagent (including the labeled reagent) in assays designed to quantitatively determine levels of the protein (or its binding partner or ligand) in biological fluids; to metabolize compounds for toxicity studies; and as markers for tissues in which the corresponding protein is preferentially expressed (either constitutively or at a particular stage of tissue differentiation or development or in a disease state). Where the protein binds or potentially binds to another protein or ligand (such as, for example, in a enzyme-effector protein interaction or enzyme-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the proteins of the present invention are based primarily on the source of the protein as well as the class/action of the protein. For example, proteins related to members of the sulfotransferase proteins are typically drug-metabolizing enzymes and serve as targets for identifying agents for use in mammalian therapeutic applications, e.g. a human drug, particularly in modulating a biological or pathological response in a cell or tissue that expresses the protein of the present invention. Experimental data provided in FIG. 1 shows that the proteins of the present invention are expressed at least in the kidney and small intestine. Specifically, multiple cDNA libraries were screened and positive clones were retrieved from libraries generated from mRNA isolated from these tissues. A large percentage of pharmaceutical agents are being developed that modulate the activity of proteins, particularly members of the sulfotransferase subfamily (see Background of the Invention) and proteins that are expressed in the kidney and intestine (killing cancer calls of these tissues that express these proteins). The structural and functional information provided in the Background and Figures provide specific and substantial uses for the molecules of the present invention, particularly in combination with the expression information provided in FIG. 1. Experimental data provided in FIG. 1 shows that the sulfotransferase of the present invention is expressed at least in the kidney and small intestine. Further, the proteins of the present invention can be used in an industrial setting to label agents with tagged sulfur. Such uses can readily be determined using the information provided herein, that which is known in the art, and routine experimentation.

The proteins of the present invention (including variants and fragments that may have been disclosed prior to the present invention) are useful for biological assays related to proteins that are related to members of the sulfotransferase subfamily. Such assays involve any of the known drug-metabolizing enzyme functions or activities or properties useful for diagnosis and treatment of drug-metabolizing enzyme-related conditions that are specific for the subfamily of drug-metabolizing enzymes that the one of the present invention belongs to, particularly in cells and tissues that express the drug-metabolizing enzyme. Experimental data provided in FIG. 1 shows that the sulfotransferase of the present invention is expressed at least in the kidney and small intestine. Specifically, multiple cDNA libraries were screened and positive clones were retrieved from libraries generated from mRNA isolated from these tissues.

The proteins of the present invention are also useful in labeling target agents with tagged sulfur. Such uses are readily apparent based on the enzymatic properties of the proteins of the present invention.

The proteins of the present invention are also useful in drug screening assays, in cell-based or cell-free systems. Cell-based systems can be native, i.e., cells that normally express the protein of the present invention, as a biopsy or expanded in cell culture. Experimental data provided in FIG. 1 shows that the sulfotransferase of the present invention is expressed at least in the kidney and small intestine. In an alternate embodiment, cell-based assays involve recombinant host cells expressing the protein of the present invention.

The polypeptides can be used to identify compounds that modulate the activity of the protein in its natural state or an altered form that causes a specific disease or pathology associated with the protein. Both the protein of the present invention and appropriate variants and fragments can be used in high-throughput screens to assay candidate compounds for the ability to bind to the protein of the present invention. These compounds can be further screened against a functional protein of the present invention to determine the effect of the compound on the protein's activity. Further, these compounds can be tested in animal or invertebrate systems to determine activity/effectiveness. Compounds can be identified that activate (agonist) or inactivate (antagonist) the protein of the present invention to a desired degree. Further, antagonists can be used to quench chemical reactions of the protein (e.g. a labeling step).

Further, the proteins of the present invention can be used to screen a compound for the ability to stimulate or inhibit interaction between the protein and a molecule that normally interacts with the protein. Such assays typically include the steps of combining the protein of the present invention with a candidate compound under conditions that allow the protein of the present invention, or fragment, to interact with the target molecule, and to detect the formation of a complex between the protein and the target or to detect the biochemical consequence of the interaction with the protein of the present invention and the target.

Candidate compounds include, for example, 1) peptides such as soluble peptides, including, Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the protein that competes for substrate binding. Other candidate compounds include mutant proteins or appropriate fragments containing mutations that affect protein function and thus compete for substrate. Accordingly, a fragment that competes for substrate, for example with a higher affinity, or a fragment that binds substrate but does not allow release, is encompassed by the invention.

Any of the biological or biochemical functions mediated by the protein of the present invention can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the protein of the present invention can be assayed. Experimental data provided in FIG. 1 shows that the sulfotransferase of the present invention is expressed at least in the kidney and small intestine. Specifically, multiple cDNA libraries were screened and positive clones were retrieved from libraries generated from mRNA isolated from these tissues.

Binding and/or activating compounds can also be screened by using chimeric protein of the present invention in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native protein of the present invention. Accordingly, a different set of signal transduction components is available as an end-point assay for activation. This allows for assays to be performed in other than the specific host cell from which the protein of the present invention is derived.

The proteins of the present invention are also useful in competition binding assays in methods designed to discover compounds that interact with the protein of the present invention (e.g. binding partners and/or ligands). Thus, a compound is exposed to a protein of the present invention under conditions that allow the compound to bind or to otherwise interact with the polypeptide. Soluble protein of the present invention polypeptide is also added to the mixture. If the test compound interacts with the soluble protein of the present invention polypeptide, it decreases the amount of complex formed or activity from the protein of the present invention target. This type of assay is particularly useful in cases in which compounds are sought that interact with specific regions of the protein of the present invention. Thus, the soluble polypeptide that competes with the target protein of the present invention region is designed to contain peptide sequences corresponding to the region of interest.

To perform cell free drug screening assays, it is sometimes desirable to immobilize either the protein of the present invention, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of protein of the present invention-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a protein of the present invention-binding protein and a candidate compound are incubated in the protein of the present invention-presenting wells and the amount of complex trapped in the well can be quantitated. Methods for detecting such complexes, in addition to those described above for the GST-immobilized complexes, include immunodetection of complexes using antibodies reactive with the protein of the present invention target molecule, or which are reactive with protein of the present invention and compete with the target molecule, as well as enzyme-linked assays which rely on detecting an enzymatic activity associated with the target molecule.

Agents that modulate one of the proteins of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of protein of the present invention activity identified according to these drug screening assays can be used to treat a subject with a disorder mediated by the protein of the present invention pathway, by treating cells or tissues that express the protein of the present invention. Experimental data provided in FIG. 1 shows that the sulfotransferase of the present invention is expressed at least in the kidney and small intestine. These methods of treatment include the steps of administering a modulator of protein of the present invention activity in a pharmaceutical composition to a subject in need of such treatment, the modulator being identified as described herein.

In yet another aspect of the invention, the protein of the present inventions can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1 993) Biotechniques 14:920–924; Iwabuchi et al. (1993) Oncogene 8:1693–1696; and Brent WO94/10300), to identify other proteins, which bind to or interact with the protein of the present invention and are involved in the protein's enzymatic activity.

The two-hybrid system is based on the modular nature of most transcription factors, which consist of separable DNA-binding and activation domains. Briefly, the assay utilizes two different DNA constructs. In one construct, the gene that codes for a protein of the present invention is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in viva, forming a protein of the present invention-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the protein of the present invention.

This invention further pertains to novel agents identified by the above-described screening assays. Accordingly, it is within the scope of this invention to further use an agent identified as described herein in an appropriate animal model. For example, an agent identified as described herein (e.g., a protein of the present invention-modulating agent, an antisense protein of the present invention nucleic acid molecule, a protein of the present invention-specific antibody, or a protein of the present invention-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data provided in FIG. 1 shows that the sulfotransferase of the present invention is expressed at least in the kidney and small intestine. The method involves contacting a biological sample with a compound capable of interacting with the protein of the present invention such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The proteins of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered protein of the present invention activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the protein of the present invention in which one or more of the protein of the present invention functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and protein of the present invention activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data provided in FIG. 1 shows that the sulfotransferase of the present invention is expressed at least in the kidney and small intestine. Accordingly, methods for treatment include the use of the protein of the present invention or fragments.

Antibodies

The invention also provides antibodies that selectively bind to one of the proteins of the present invention, a protein comprising a fragment of such a protein, as well as variants and fragments thereof. As used herein, an antibody selectively binds a target protein or peptide when it binds the target peptide and does not significantly bind to unrelated peptides or proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in teems consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the protein of the present invention. Antibodies can be prepared from any region of the peptide as described herein. However, preferred regions will include those involved in function/activity and/or protein/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data provided in FIG. 1 shows that the sulfotransferase of the present invention is expressed at least in the kidney and small intestine. Specifically, multiple cDNA libraries were screened and positive clones were retrieved from libraries generated from mRNA isolated from these tissues. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full-length protein can be used to identify protein turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data provided in FIG. 1 shows that the sulfotransferase of the present invention is expressed at least in the kidney and small intestine. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data provided in FIG. 1 shows that the sulfotransferase of the present invention is expressed at least in the kidney and small intestine. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data provided in FIG. 1 shows that the sulfotransferase of the present invention is expressed at least in the kidney and small intestine. Thus, where a specific protein has been correlated with expression in a specific tissue, antibodies that are specific for this protein can be used to identify a tissue type.

The antibodies are also useful for inhibiting protein function, for example, blocking the binding of the protein to a binding partner such as a substrate. These uses can also be applied in a therapeutic context in which treatment involves inhibiting the protein's function. An antibody can be used, for example, to block binding, thus modulating (agonizing or antagonizing) the protein's activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nucleic acids but similar methods have been developed for antibody arrays.

Nucleic Acid Molecules

The present invention further provides isolated nucleic acid molecules that encode a protein of the present invention (cDNA, transcript and genomic sequence). Such nucleic acid molecules will consist of, consist essentially of, or comprise a nucleotide sequence that encodes one of the proteins of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NOS:1 and 2, alternative transcript sequences, and SEQ ID NO:3, cDNA sequences, transcript sequence and SEQ ID NO:3, genomic sequence), or any nucleic acid molecule that encodes the protein provided in FIG. 2, SEQ ID NOS:4–6. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NOS:1 and 2, alternative transcript sequences, and SEQ ID NO:3, cDNA sequences, transcript sequence and SEQ ID NO:3, genomic sequence), or any nucleic acid molecule that encodes the protein provided in FIG. 2, SEQ ID NOS:4–6. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NOS:1 and 2, alternative transcript sequences, and SEQ ID NO:3, cDNA sequences, transcript sequence and SEQ ID NO:3, genomic sequence), or any nucleic acid molecule that encodes the protein provided in FIG. 2, SEQ ID NOS:4–6. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the proteins of the present invention alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule maybe fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the proteins of the present invention as well as nucleic acid molecules that encode obvious variants of the proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100 s or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a regional of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the map position was determined to be on chromosome 2 near marker SHGC-1639 (LOD score 10.01) using radiation hybrid mapping.

FIG. 3 provides SNP information that was identified from chromosomal sequence obtained from a number of individuals as well as SNPs found during the cDNA cloning process. These include, a6094g, t7898c, a10018c, a10791t, a12451t, t14674c, g14860c, a20133g, a1025e, t12602c, g12829t, a1442t.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in Current Protocols in Molecular Biology, John Wiley & Sons, NY (1989), 6.3.1–6.3.6. One example of stringent hybridization conditions are hybridization in 6× sodium chloride/sodium citrate (SSC) at about 45C, followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, mapping reagents, expression control reagents and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, identified SNP variations include a1008c, a6094g, t7898c, a10018c, a10791t, a12451t, t14674c, g14860c, a20133g, a1025c, t12602c, g12829t, a1442t.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence. Such molecules are useful in genotyping and mapping experiments, particularly if the probed region contains one or more of the sequence variants described herein.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 2 near marker SHGC-1639 (LOD score 10.01) using radiation hybrid mapping. Further, the SNP variants provided herein can be used in mapping and linkage studies.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data provided in FIG. 1 shows that the sulfotransferase of the present invention is expressed at least in the kidney and small intestine. Specifically, multiple cDNA libraries were screened and positive clones were retrieved from libraries generated from mRNA isolated from these tissues. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a protein of the present invention, such as by measuring a level of a protein of the present invention-encoding nucleic acid ill a sample of cells from a subject e.g., mRNA or genomic DNA, or determining if a protein of the present invention gene has been mutated. Experimental data provided in FIG. 1 shows that the sulfotransferase of the present invention is expressed at least in the kidney and small intestine. Specifically, multiple cDNA libraries were screened and positive clones were retrieved from libraries generated from mRNA isolated from these tissues.

Nucleic acid expression assays are useful for drug screening to identify compounds that modulate protein of the present invention nucleic acid expression.

The invention thus provides a method for identifying a compound that can be used to treat a disorder associated with nucleic acid expression of the protein of the present invention gene, particularly biological and pathological processes that are mediated by the protein of the present invention in cells and tissues that express it. Experimental data provided in FIG. 1 shows that the sulfotransferase of the present invention is expressed at least in the kidney and small intestine. The method typically includes assaying the ability of the compound to modulate the expression of the protein of the present invention nucleic acid and thus identifying a compound that can be used to treat a disorder characterized by undesired protein of the present invention nucleic acid expression. The assays can be performed in cell-based and cell-free systems. Cell-based assays include cells naturally expressing the protein of the present invention nucleic acid or recombinant cells genetically engineered to express specific nucleic acid sequences.

Thus, modulators of protein of the present invention gene expression can be identified in a method wherein a cell is contacted with a candidate compound and the expression of mRNA determined. The level of expression of protein of the present invention mRNA in the presence of the candidate compound is compared to the level of expression of protein of the present invention mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate protein of the present invention nucleic acid expression in cells and tissues that express the protein. Experimental data provided in FIG. 1 shows that the sulfotransferase of the present invention is expressed at least in the kidney and small intestine. Specifically, multiple cDNA libraries were screened and positive clones were retrieved from libraries generated from mRNA isolated from these tissues. Modulation includes both up-regulation (i.e. activation or agonization) or down-regulation (suppression or antagonization) or nucleic acid expression.

Alternatively, a modulator for nucleic acid expression can be a small molecule or drug identified using the screening assays described herein as long as the drug or small molecule inhibits the protein of the present invention nucleic acid expression in the cells and tissues that express the protein. Experimental data provided in FIG. 1 shows that the sulfotransferase of the present invention is expressed at least in the kidney and small intestine.

The nucleic acid molecules are also useful for monitoring the effectiveness of modulating compounds on the expression or activity of the protein of the present invention gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in protein of the present invention nucleic acid expression, and particularly in qualitative changes that lead to pathology. The nucleic acid molecules can be used to detect mutations in protein of the present invention genes and gene expression products such as mRNA. The nucleic acid molecules can be used as hybridization probes to detect naturally occurring genetic mutations in the protein of the present invention gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the protein of the present invention gene associated with a dysfunction provides a diagnostic tool for an active disease or susceptibility to disease when the disease results from overexpression, underexpression, or altered expression of a protein of the present invention.

Individuals carrying mutations in the protein of the present invention gene can be detected at the nucleic acid level by a variety of techniques. FIG. 3 provides SNP information that was identified from chromosomal sequence obtained from a number of individuals as well as SNPs found during the cDNA cloning process. These include, a6094g, t7898c, a10018c, a10791t, a12451t, t14674c, g14860c, a20133g, a1025c, t12602c, g12829t, a1442t. As indicated by the data presented in FIG. 3, the map position was determined to be on chromosome 2 near marker SHGC-1639 (LOD score 10.01) using radiation hybrid mapping. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a protein of the present invention gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant protein of the present invention gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment, (pharmacogenomic relationship). Accordingly, the nucleic acid molecules described herein can be used to assess the mutation content of the protein of the present invention gene in an individual in order to select an appropriate compound or dosage regimen for treatment. FIG. 3 provides SNP information that was identified from chromosomal sequence obtained from a number of individuals as well as SNPs found during the cDNA cloning process. These include, a6094g, t7898c, a10018c, a10791t, a12451t, t14674c, g14860c, a20133g, a1025c, t12602c, g12829t, a1442t.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control protein of the present invention gene expression in cells, tissues, and organisms. A DNA antisense nucleic acid molecule is designed to be complementary to a region of the gene involved in transcription, preventing transcription and hence production of protein of the present invention. An antisense RNA or DNA nucleic acid molecule would hybridize to the mRNA and thus block translation of mRNA into a protein of the present invention.

Alternatively, a class of antisense molecules can be used to inactivate mRNA in order to decrease expression of protein of the present invention nucleic acid. Accordingly, these molecules can treat a disorder characterized by abnormal or undesired protein of the present invention nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities or the protein of the present invention, such as substrate binding.

The nucleic acid molecules also provide vectors for gene therapy in patients containing cells that are aberrant in gene expression. Thus, recombinant cells which include the patient's cells that have been engineered ex vivo and returned to the patient, are introduced into an individual where the cells produce the desired protein of the present invention to treat the individual.

The invention also encompasses kits for detecting the presence of a protein of the present invention encoding nucleic acid in a biological sample. Experimental data provided in FIG. 1 shows that the sulfotransferase of the present invention is expressed at least in the kidney and small intestine. Specifically, multiple cDNA libraries were screened and positive clones were retrieved from libraries generated from mRNA isolated from these tissues. For example, the kit can comprise reagents such as a labeled or labelable nucleic acid or agent capable of detecting protein of the present invention encoding nucleic acid in a biological sample; means for determining the amount of protein of the present invention encoding nucleic acid in the sample; and means for comparing the amount of protein of the present invention encoding nucleic acid in the sample with a standard. The compound or agent can be packaged in a suitable container. The kit can further comprise instructions for using the kit to detect a protein of the present invention mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,599.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described alcove, may be produced by hand or by using available devices (slot blot or dot blot apparatus), materials (any suitable solid support), and machines (including, robotic instruments), and may contain 8, 94, 96, 384, 1536, 6144 or more oligonucleotides, or any other number between two and one million which lends itself to the efficient use of commerically available instrumentation.

In order to Conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the proteins of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the protein of the present invention encoding gene of the present invention. FIG. 3 provides SNP information that was identified from chromosomal sequence obtained from a number of individuals as well as SNPs found during the cDNA cloning process. These include, a6094g, t7898c, a10018c, a1079t, a12451t, t14674c, g14860c, a20133g, a1025c, t12602c, g12829t, a1442t Conditions For incubating a nucleic acid molecule with a test sample vary Incubation conditions depend on the format employed in the assay, the detection methods employed, and the type and nature of the nucleic acid molecule used in, the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based oil the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified protein of the present invention encoding gene of the present invention can be routinely identified using the sequence information disclosed herein can be readily incorporated into one of the established kit formats which are well known in the art, particularly expression arrays.

Vectors/host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, Such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al, *Molecular Cloning: A Laboratory Manual*. 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook, et al, *Molecular Cloning, A Laboratory Mannual*, 2nd ed, Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing, for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli, Streptomyces*, and *Salmonella typhimurium*. Eukaryotic cells include, but are not limited to, yeast, insect cells such as *Drosophila*, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRTT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185,60–89 (1990)).

Recombinant protein expression can be maximized in host bacteria by providing a genetic background wherein the host cell has an impaired capacity to protocolytically cleave the recombinant protein (Gottesman, S., *Gene Expression Technology Methods in Enzymology* 185, Academic Press, San Diego, Calif. (1990) 119–128). Alternatively, the sequence or the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcriptional of antisense RNA. Thus, an antisense transcript can be produced to all, or to a portion, of the nucleic acid molecule sequences described herein, including both coding and non-cod regions. Expression of this antisense RNA, is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Mannual,* 2nd, ed., Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained the the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, appropriate secretion signals are incorporated into the vector. The signal sequence can be endogenous to the peptides or heterologous to these peptides.

Where the peptide is not secreted into the medium, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a protein of the present invention or peptide that can be further purified to produce desired amounts of a protein of the present invention or fragments. Thus, host cells containing expression vectors are useful for peptide production.

Host cells are also useful for conducting cell-based assays involving the protein of the present invention or fragments, such as those described above as well as other formats known in the art. Thus, recombinant host cell expressing a native protein of the present invention is useful for assaying compounds that stimulate or inhibit a protein of the present invention function.

Host cells are also useful for identifying mutants in which these functions are affected. If the mutants naturally occur and give rise to a pathology, host cells containing the mutations are useful to assay compounds that have a desired effect on the mutant protein of the present invention (for example, stimulating or inhibiting function) which may not be indicated by their effect on the native protein of the present invention.

Genetically engineered host cells can be further used to produce non-human transgenic animals. A transgenic animal is preferably a mammal, for example a rodent, such as a rat or mouse, in which one or more of the cells of the animal include a transgenic. A transgene is exogenous DNA which is integrated into the genome of a cell from which a transgenic animal develops and which remains in the genome of the mature animal in one or more cell types or tissues of the transgenic animal. These animals are useful for studying the function of a protein of the present invention and identifying and evaluating modulators of protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the protein of the present invention encoding nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the protein of the present invention to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al., and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in Vehicle the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. el al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an nucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, protein activation, and signal transduction, may not be evident from in vitro cell-free or cell-based assays. Accordingly, it is useful to provide non-human transgenic animals to assay in vivo protein function, including substrate interaction, the effect of specific mutant proteins on protein function and substrate interaction, and the effect of chimeric protein of the present invention. It is also possible to assess the effect of null mutations, that is mutations that substantially or completely eliminate one or more of the proteins functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule consisting of a nucleotide sequence encoding a phenol sulfotransferase protein selected from the group consisting of:
   (a) a nucleotide sequence that encodes a protein comprising the amino acid sequence of SEQ ID NO: 5; and
   (b) a nucleotide sequence consisting of the nucleic acid sequence of SEQ ID NO: 2.

2. A nucleic acid vector comprising a nucleic acid molecule of claim 1.

3. A host cell containing the vector of claim 2.

4. A method for producing a polypeptide comprising culturing the host cell of claim 3 under conditions sufficient for the production of said polypeptide, and recovering the peptide from the host cell culture.

5. A method for detecting the presence of a nucleic acid molecule of claim 1 in a sample, said method comprising contacting the sample with an oligonucleotide comprising at least 20 contiguous nucleotides that hybridizes to said nucleic acid molecule under stringent conditions, wherein the stringent conditions is hybridization in 6× sodium chloride/sodium citrate (SSC) at about 45° C., followed by one or more washes in 0.2×SSC, 0.1% SDS al 50–65° C., and determining whether the oligonucleotide binds to said nucleic acid molecule in the sample.

6. An isolated nucleic acid molecule consisting of a nucleotide sequence that is completely complementary to a nucleotide sequence of claim 1.

7. An isolated polynucleotide consisting of a nucleotide sequence set forth in SEQ ID NO: 2.

8. An isolated nucleic acid molecule comprising a nucleotide sequence encoding a phenol sulfotransferase protein selected from the group consisting of:
   (a) a nucleotide sequence that encodes a protein comprising the amino acid sequence of SEQ ID NO: 5; and
   (b) a nucleotide sequence comprising SEQ ID NO: 2.

9. A nucleic acid vector comprising a nucleic acid molecule of claim 8.

10. A host cell containing the vector of claim 9.

11. A vector according to claim 9, wherein said vector is selected from the group consisting of a plasmid, virus, and bacteriophage.

12. A vector according to claim 9, wherein said isolated nucleic acid molecule is inserted into said vector in proper orientation and correct reading frame such that the protein of SEQ ID NO: 5 may be expressed by a cell transformed with said vector.

13. A vector according to claim 12, wherein said isolated nucleic acid molecule is operatively linked to a promoter sequence.

14. An isolated nucleic acid molecule comprising a nucleotide sequence that is completely complementary to a nucleotide sequence of claim 8.

* * * * *

SEQUENCE LISTING

<160> NUMBER OF SEQ ID NOS: 23

<210> SEQ ID NO 1
<211> LENGTH: 942
<212> TYPE: DNA
<213> ORGANISM: Homo sapiens

<400> SEQUENCE: 1

```
attcccaatg gcgaagattg agaaaaacgc tcccacgatg gaaaaaaagc cagaactgtt      60
taacatcatg gaagtagatg gagtccctac gttgatatta tcaaaagaat ggtgggaaaa     120
agtatgtaat ttccaagcca agcctgatga tcttattctg gcaacttacc caaagtcagg     180
tacaacatgg atgcatgaaa ttttagacat gattctaaat gatggtgatg tggagaaatg     240
caaaagagcc cagactctag atagacacgc tttccttgaa ctgaaatttc cccataaaga     300 aaaccagat ttggagttcg ttcttgaaat gtcctcacca caactgataa aaacacatct     360
cccttcacat ctgattccac catctatctg gaaagaaaac tgcaagattg tctatgtggc     420
cagaaatccc aaggattgcc tggtgtccta ctaccacttt cacaggatgg cttcctttat     480
gcctgatcct cagaacttag aggaatttta tgagaaattc atgtccggaa aagttgttgg     540
cgggtcctgg tttgaccatg tgaaaggatg gtgggctgca aaagacatgc accggatcct     600
ctacctcttc tacgaggata ttaaaaaaaa tccaaaacat gagatccaca aggtgttgga     660
attcttggag aaaacttggt caggtgatgt tataaacaag attgtccacc atacctcatt     720
tgatgtaatg aaggataatc ccatggccaa ccatactgcg gtacctgctc acatattcaa     780
tcactccatc tcaaaattta tgaggaaagg gatgcctgga gactggaaga accactttac     840
tgtggctttg aatgagaact ttgataagca ttatgaaaag aagatggcag gtccacact      900 gaacttctgc ctggagatct gagaggaaca acaacaaact ag                        942
```

<210> SEQ ID NO 2
<211> LENGTH: 922
<212> TYPE: DNA
<213> ORGANISM: Homo sapiens

<400> SEQUENCE: 2

```
attcccaatg gcgaagattg agaaaaacgc tcccacgatg gaaaaaaagc cagaactgtt      60
taacatcatg gaagtagatg gagtccctac gttgatatta tcaaaagaat ggtgggaaaa     120
agtatgtaat ttccaagcca agcctgatga tcttattctg gcaacttacc caaagtcagg     180
tacaacatgg atgcatgaaa ttttagacat gattctaaat gatggtgatg tggagaaatg     240
```

```
caaaagagcc cagactctag atagacacgc tttccttgaa ctgaaatttc cccataaaga      300
aaaaccagat ttggagttcg ttcttgaaat gtcctcacca caactgataa aaacacatct      360
cccttcacat ctgattccac catctatctg gaaagaaaac tgcaagattg tctatgtggc      420
cagaaatccc aaggattgcc tggtgtccta ctaccacttt cacaggatgg cttcctttat      480
gcctgatcct cagaacttag aggaatttta tgagaaattc atgtccggaa aagttgttgg      540
cgggtcctgg tttgaccatg tgaaaggatg gtgggctgca aaagacatgc accggatcct      600
ctacctcttc tacgaggata ttaaaaaaga cccaaagcgg gaaattgaga agatactgaa      660
gttcctggaa aaagacatat cagaggaaat tctgaataaa atcatctatc acctccctt      720 tgatgtaatg aagcaaaacc caatgaccaa ctataccact ttgcccacca gcattatgga      780
ccactccatc tccccttta tgaggaaagg gatgcctgga gactggaaga actatttac        840 tgtggcccaa aatgaagaat ttgacaagga ctaccagaag aagatggcag gaagcaccct      900
aaccttccgc acagagatct ga                                               922

<210> SEQ ID NO 3
<211> LENGTH: 1004
<212> TYPE: DNA
<213> ORGANISM: Homo sapiens

<400> SEQUENCE: 3
ctcactatta gggcgaattg aatttagcgg ccgcgaattc gcccttatgg cgaagattga       60 gaaaacgct cccacgatgg aaaaaaagcc agaactgttt aacatcatgg aagtagatgg       120
agtccctacg ttgatattat caaagaatg gtgggaaaaa gtctgtaatt ccaagccaa        180 gcctgatgat cttattctgg caacttaccc aaagtcaggt acaacatgga tgcatgaaat      240
tttagacatg attctaaatg atggtgatgt ggagaaatgc aaaagagccc agactctaga      300
tagacacgct ttccttgaac tgaaattccc cataaagaa aaaccagatt tggagttcgt       360
tcttgaaatg tcctcaccac aactgataaa aacacatctc ccttcacatc tgattccacc      420
atctatctgg aaagaaaact gcaagattgt ctatgtggcc agaaatccca aggattgcct      480
ggtgtcctac taccactttc acaggatggc ttcctttatg cctgatcctc agaacttaga      540
ggaattttat gagaaattca tgtccggaaa agttgttggc gggtcctggt ttgaccatgt      600
gaaaggatgg tgggctgcaa agacacgca ccggatcctc tacctcttct acgaggatat       660 taaaaaaat ccaaacatg agatccacaa ggtgttggaa ttcttggaga aactttgtc         720 aggtgatgtt ataaacaaga ttgtccacca tacctcattt gatgtaatga aggataatcc      780
catggccaac catactgcgg tacctgctca catattcaat cactccatct caaaatttat      840
gaggaaaggg atgcctggag actggaagaa ccactttact gtggctatga atgagaactt      900
tgataagcat tatgaaaaga gatggcaggt ccacactg aacttctgcc tggagatctg        960
agaggaacaa caaagggcga attcgtttaa acctgcagga ctag                      1004

<210> SEQ ID NO 4
<211> LENGTH: 304
<212> TYPE: PRT
<213> ORGANISM: Homo sapiens

<400> SEQUENCE: 4

Met Ala Lys Ile Glu Lys Asn Ala Pro Thr Met Glu Lys Lys Pro Glu
 1               5                  10                  15

Leu Phe Asn Ile Met Glu Val Asp Gly Val Pro Thr Leu Ile Leu Ser
```

-continued

```
                20                  25                  30
Lys Glu Trp Trp Glu Lys Val Cys Asn Phe Gln Ala Lys Pro Asp Asp
            35                  40                  45

Leu Ile Leu Ala Thr Tyr Pro Lys Ser Gly Thr Thr Trp Met His Glu
        50                  55                  60

Ile Leu Asp Met Ile Leu Asn Asp Gly Asp Val Glu Lys Cys Lys Arg
65                  70                  75                  80

Ala Gln Thr Leu Asp Arg His Ala Phe Leu Glu Leu Lys Phe Pro His
                85                  90                  95

Lys Glu Lys Pro Asp Leu Glu Phe Val Leu Glu Met Ser Ser Pro Gln
            100                 105                 110

Leu Ile Lys Thr His Leu Pro Ser His Leu Ile Pro Pro Ser Ile Trp
        115                 120                 125

Lys Glu Asn Cys Lys Ile Val Tyr Val Ala Arg Asn Pro Lys Asp Cys
    130                 135                 140

Leu Val Ser Tyr Tyr His Phe His Arg Met Ala Ser Phe Met Pro Asp
145                 150                 155                 160

Pro Gln Asn Leu Glu Glu Phe Tyr Glu Lys Phe Met Ser Gly Lys Val
                165                 170                 175

Val Gly Gly Ser Trp Phe Asp His Val Lys Gly Trp Trp Ala Ala Lys
            180                 185                 190

Asp Met His Arg Ile Leu Tyr Leu Phe Tyr Glu Asp Ile Lys Lys Asn
        195                 200                 205

Pro Lys His Glu Ile His Lys Val Leu Glu Phe Leu Glu Lys Thr Trp
    210                 215                 220

Ser Gly Asp Val Ile Asn Lys Ile Val His His Thr Ser Phe Asp Val
225                 230                 235                 240

Met Lys Asp Asn Pro Met Ala Asn His Thr Ala Val Pro Ala His Ile
                245                 250                 255

Phe Asn His Ser Ile Ser Lys Phe Met Arg Lys Gly Met Pro Gly Asp
            260                 265                 270

Trp Lys Asn His Phe Thr Val Ala Leu Asn Glu Asn Phe Asp Lys His
        275                 280                 285

Tyr Glu Lys Lys Met Ala Gly Ser Thr Leu Asn Phe Cys Leu Glu Ile
    290                 295                 300

<210> SEQ ID NO 5
<211> LENGTH: 304
<212> TYPE: PRT
<213> ORGANISM: Homo sapiens

<400> SEQUENCE: 5

Met Ala Lys Ile Glu Lys Asn Ala Pro Thr Met Glu Lys Lys Pro Glu
1               5                   10                  15

Leu Phe Asn Ile Met Glu Val Asp Gly Val Pro Thr Leu Ile Leu Ser
                20                  25                  30

Lys Glu Trp Trp Glu Lys Val Cys Asn Phe Gln Ala Lys Pro Asp Asp
            35                  40                  45

Leu Ile Leu Ala Thr Tyr Pro Lys Ser Gly Thr Thr Trp Met His Glu
        50                  55                  60

Ile Leu Asp Met Ile Leu Asn Asp Gly Asp Val Glu Lys Cys Lys Arg
65                  70                  75                  80

Ala Gln Thr Leu Asp Arg His Ala Phe Leu Glu Leu Lys Phe Pro His
                85                  90                  95
```

-continued

```
Lys Glu Lys Pro Asp Leu Glu Phe Val Leu Glu Met Ser Ser Pro Gln
            100                 105                 110

Leu Ile Lys Thr His Leu Pro Ser His Leu Ile Pro Pro Ser Ile Trp
            115                 120                 125

Lys Glu Asn Cys Lys Ile Val Tyr Val Ala Arg Asn Pro Lys Asp Cys
        130                 135                 140

Leu Val Ser Tyr Tyr His Phe His Arg Met Ala Ser Phe Met Pro Asp
145                 150                 155                 160

Pro Gln Asn Leu Glu Glu Phe Tyr Glu Lys Phe Met Ser Gly Lys Val
                165                 170                 175

Val Gly Gly Ser Trp Phe Asp His Val Lys Gly Trp Trp Ala Ala Lys
            180                 185                 190

Asp Met His Arg Ile Leu Tyr Leu Phe Tyr Glu Asp Ile Lys Lys Asp
        195                 200                 205

Pro Lys Arg Glu Ile Glu Lys Ile Leu Lys Phe Leu Glu Lys Asp Ile
    210                 215                 220

Ser Glu Glu Ile Leu Asn Lys Ile Ile Tyr His Thr Ser Phe Asp Val
225                 230                 235                 240

Met Lys Gln Asn Pro Met Thr Asn Tyr Thr Thr Leu Pro Thr Ser Ile
                245                 250                 255

Met Asp His Ser Ile Ser Pro Phe Met Arg Lys Gly Met Pro Gly Asp
            260                 265                 270

Trp Lys Asn Tyr Phe Thr Val Ala Gln Asn Glu Glu Phe Asp Lys Asp
        275                 280                 285

Tyr Gln Lys Lys Met Ala Gly Ser Thr Leu Thr Phe Arg Thr Glu Ile
    290                 295                 300
```

<210> SEQ ID NO 6
<211> LENGTH: 304
<212> TYPE: PRT
<213> ORGANISM: Homo sapiens

<400> SEQUENCE: 6

```
Met Ala Lys Ile Glu Lys Asn Ala Pro Thr Met Glu Lys Lys Pro Glu
1               5                   10                  15

Leu Phe Asn Ile Met Glu Val Asp Gly Val Pro Thr Leu Ile Leu Ser
            20                  25                  30

Lys Glu Trp Trp Glu Lys Val Cys Asn Phe Gln Ala Lys Pro Asp Asp
        35                  40                  45

Leu Ile Leu Ala Thr Tyr Pro Lys Ser Gly Thr Thr Trp Met His Glu
    50                  55                  60

Ile Leu Asp Met Ile Leu Asn Asp Gly Asp Val Glu Lys Cys Lys Arg
65                  70                  75                  80

Ala Gln Thr Leu Asp Arg His Ala Phe Leu Glu Leu Lys Phe Pro His
                85                  90                  95

Lys Glu Lys Pro Asp Leu Glu Phe Val Leu Glu Met Ser Ser Pro Gln
            100                 105                 110

Leu Ile Lys Thr His Leu Pro Ser His Leu Ile Pro Pro Ser Ile Trp
            115                 120                 125

Lys Glu Asn Cys Lys Ile Val Tyr Val Ala Arg Asn Pro Lys Asp Cys
        130                 135                 140

Leu Val Ser Tyr Tyr His Phe His Arg Met Ala Ser Phe Met Pro Asp
145                 150                 155                 160

Pro Gln Asn Leu Glu Glu Phe Tyr Glu Lys Phe Met Ser Gly Lys Val
                165                 170                 175
```

```
Val Gly Gly Ser Trp Phe Asp His Val Lys Gly Trp Trp Ala Ala Lys
            180                 185                 190

Asp Thr His Arg Ile Leu Tyr Leu Phe Tyr Glu Asp Ile Lys Lys Asn
            195                 200                 205

Pro Lys His Glu Ile His Lys Val Leu Glu Phe Leu Glu Lys Thr Leu
            210                 215                 220

Ser Gly Asp Val Ile Asn Lys Ile Val His His Thr Ser Phe Asp Val
225                 230                 235                 240

Met Lys Asp Asn Pro Met Ala Asn His Thr Ala Val Pro Ala His Ile
                245                 250                 255

Phe Asn His Ser Ile Ser Lys Phe Met Arg Lys Gly Met Pro Gly Asp
            260                 265                 270

Trp Lys Asn His Phe Thr Val Ala Met Asn Glu Asn Phe Asp Lys His
            275                 280                 285

Tyr Glu Lys Lys Met Ala Gly Ser Thr Leu Asn Phe Cys Leu Glu Ile
            290                 295                 300

<210> SEQ ID NO 7
<211> LENGTH: 20165
<212> TYPE: DNA
<213> ORGANISM: Homo sapiens

<400> SEQUENCE: 7
agttccaaac tttcccacat tttcctgtct tcttctgttc caatctctgc ctgttaccca      60
gttccaaagt caattttaca tttttcaggta tctgcagtag caccccactc tgctagtaca    120
aatttattgt attagtccct tttcatgctg ttaataaaga catacctgag actgggcaat    180
ttaaaaaata acgaggttta acagacttaa agttccacgt atctgggaa gcctcacagt      240
catggtggaa ggcaatgaat ggcagcaggc aaaggaaaag agagcttgtg caggggaact    300
cccccttata atgggtgggg acacaggcga accatatcag accccaacta aattccaagt    360
ttccagagtt agtagacatg agagttttca ggtacatggg tacaagagag tttttttctgc   420
tgtaacccat gactgatatt tcaaaaatta ttccatgaat gaaaaaaaaa ctacatgaaa    480
ttatgttttt tgaagatttt ctctgtgaaa actattcaag aaaattgagt atagaatgct    540
ccttaaaacc attgttttga atttcttca atgtaattgt ctcgcttcta attatacaaa      600
ataatatctt gaagacaatg aagcaatata tgacacataa cccattatat tcccgattaa    660
caagtaatat ggttgttagg tcatgcagca ggaaaaagac tatttgggta taaatctcag    720
ccccaacagg tattgattat tttactttta tcaaattatt taaacttata atgacttaag    780
tttccacatg tagaaaacag aaaaaactat tacctatttt atgtggttgc tatgaagatt    840
aaataattaa tgtacataga gtaagttgtt agcatgttat atgttagctt tcacttattt    900
tatgctattc taatcaaagg cagtaagatg ataacccata ctatgaacca taaaacaaca    960
tttttaaaaa ttttaattag tattgatctt acccatccca gattcccaat ggcgaagatt   1020
gagaaaaacg ctcccacgat ggaaaaaaag ccagaactgt ttaacatcat ggaagtagat   1080
ggagtcccta cgttgatatt atcaaaagaa tggtgggaaa agtatgtaa tttccaagcc    1140
aagcctgatg atcttattct ggcaacttac ccaaagtcag gtaagggtag caaaacataa   1200
aaatattcaa tattttcacg tgaaattatt gcataatctg tattgataaa tgaagcatga   1260
ttgggatttg gagagaaaca attcctcatt atggagatct gttctttggt gctgcaggac   1320
atttagcatt cctgatccct aggacaacaa tttccaatag cactctctga agagaacaga   1380
```

```
aaagatttct aaatgctttg gtagtagggc agataatgct cccattccag aacccatagc   1440
atacatcaaa tataaggtca acaaattgaa agacctatgg cttttttaaa catcaaccct   1500
caagacagcc ttctaaaagc atgtcctact ccaaatatta atctattatc tcagatatta   1560
aacacaaatt gattttctaa tcctctaaag ctcttggagg atgtcagcca tgaattttct   1620
gctctgtacc aaattagtct cattcagaaa agcccaatga ctgaccttga tttaaaatgc   1680
cttagatttc taattcttct ctaaaaattc ctagactgga cacatgcta gagtcaatgg    1740 gcacacctaa tgcccagaac tcactttcga taggccattc tccattaaaa tgaaccacag   1800
ctattaggag aattgatgat cccactcttg ggaatagaat atgcaagggg aatgtactac   1860
atcttctttt tgaaggagta agtgatcagt atatattccc agaattgttt gtttgtatta   1920
aatgtctgta aaaataaagc acataata acaaaaaaat tgatgggac atgtagaagg      1980 atacaagaac caacgtgaag gggctctcac agtagccaca tttgggacag tttgagcatc   2040
caaaagaatg atcactaact gattgggaga acattaaata aaaacctcct ggtcagccat   2100
gccgaaggga caagattgga tgtgtactcc agccataata aaaaggaaa ctggataaaa    2160 tatatgaaac cactggtttc tgaccttgga tgacagttgt ctcaatcctc agactgaaga   2220
tgctttctga atagggtata gttataggt gcaaagaaa aagccatagc aaactcattg      2280
agttcaagag ccaggtgtag gagttctgag aggttgaagt ggctgctatt tgcaggtaag   2340
agtaccagac agaaggaaac tacacaaata aataccttta gatatcttta gagaggaccc   2400
ttttagttta ttgttgaatg gtagactgca cttccataga gcctatagct ccatgagatc    2460
aggcaaggaa ccaccagaaa actattagcc atataattcc tagagattat acaagcatga   2520
gagacttttg tgctccaatc aggataggat ggacagaatt ttggtcccca tgacattagt   2580
cctctgttat tacatctgcc gttatttcag attacattcc caaaaggatt ttgcagttgc   2640
tattaaacta tctaatcagc tgatattaaa atagggagta tattctggac tatcttgacg   2700
gacccagtgg aatcatgtga acaggaagtc agagagatgt ggcagaggag aaagtctgag   2760
aaatttaaag tataataaaa gttcactgca tgattataga tttaatgatg aagagagaaa   2820
gtatcaacaa aacagttatc tcaatactac agccacaagc aactgaattc tgttggcatc   2880
taggagcttg gcaaaacacc ctgaagtccc agatgagaat ggcagcccta gctgatacct   2940
tgattttagc ctagtgagac cctaaacaga ggactagcca tgttaacccc aatttctaat   3000
ctacagaaac tatgaccgaa tattcaggtg ttgttttaac tcatgaagct tgtggtaatt   3060
tgttaaccac aaagtcttca acctagaatt ccatatacc agtaaaaata atatattaaa    3120
atattactaa aaataaaggt caaagacttt ttctctgaca gcgaaaagct gaatgtgttg   3180
cccgcacagc tgcactaaaa ataaataaat aaaaagttat attaaagaaa tttattcaga   3240
gtaacagaaa ataatagtat acaaaactt attatctttc aacattccag caacacacag     3300
ttggaatatg acatttaaa aataccattg ataaaataaa tagcacctga aaacatgaaa    3360
tattcagaaa tgaacttaac aaagctgtgc atgatttgaa agtgaaaaca ctacggagag   3420
aaattgtata agacttaaat aaataaggag gcataccta tctacggatc aaaaggatca    3480
atatttttaa gatatcaact gtttcaaaat taatgtataa attcaatctc aatcacaaac   3540
tgacaaattg attccaagat ttctatgaaa atgtcattaa aagcaaatat ttttgataga   3600
gtaaagtggc agggtttata ttaactgatt tcatgacatt taactcagct tcaacattca   3660
aaagactgtg atactgttga tattgttgat agacataaat acttgaccct tacttggtgc   3720
cagatgcaaa aaagtcaaag tgcaatgcat cagacctcaa aaaattaaaa ttaaatctct   3780
```

-continued

```
aaaactatgg aagtatagat aggagaatag cttcaaactt taggttaggc aacaataatt   3840
tggggaaaaa aatggaaagc actacccttt atggtttgca tttaatgtaa attcaatata   3900
aattagactt aatcaaatta aaacttctgt tcttctaaag acccagttaa gaaaataaaa   3960
atatgtgaca tagatggaga gaaatattc acaatacata tatctggcca gaaggtataa    4020
agaactgtta caactaagaa caaaaaacaa aaaaaaaatg tattaaagtg ggcaaaagat   4080
gtaaaaatgt atcaccaaaa aagctttact attaaccaat aaacacaaga tattcaacat   4140
catttatcat gagaaaatgt aaattagtac tataatgaaa taccactaca caccacttca   4200
aatggctaaa aacctggaaa tactaagtgt tgataaggac acagagcaac tgaaattctc   4260
atgaactttt ggggaggacc taacatggta ctaatgttga acagtttgtt ataaaactaa   4320
acatgcacct accacacaac ccagcaactc caatcctaga gattcacccc caccccaaa    4380 atagaaatct atgttcatat aaaaacttgt acacaacact atagcagact tattcaaaat   4440
tagcccaaca ctgaagaaaa cctaaattcg tattgtcata taaatgaata aacaaatcac   4500
tgcttatcca tacaattgaa ctgttctcag caattaaaaa aaatgaacta cagatatata   4560
caagaacata aatgaatccc aaaataatga gggtgtgtga aaaaattcag acacatgagg   4620
acaaactgta tggtttcatt tatatgaaat tcaacaatgt gtaaaactaa tttgtattga   4680
caaaaacata gatcagcagt tccgtggagt cggaagtgag gaaaagaatt actgatagca   4740
acagacacaa cgttctactc ttatctatgg taatggctac atacatttgt caaatttcct   4800
taaactacac atttataaca ggttcattct attctatgta attttaccca cactgaagtt   4860
tatttcaaaa aacgtgattc cataatgatg aaaaatacaa aaagaaaaac ttatgtatta   4920
tgattgaaga taactgttat tcatctctta gactaaaaag aagtaattaa gagaaagaat   4980
ttagaggaat tgcagttctt ccctgattta tgagggaaag ttctttatat gaagatctac   5040
ctaataaata gagaagtgag gggattagaa aataagcaat tgaaaccca caataaaaat    5100 taggtaaagt aggatcatta atgaatgaat cttaaaataa ttagataaaa tatgaggaga   5160
actggctggt cacatggtac tgaaatgtca ccacatagtt ttattcctaa aagcaaatgg   5220
aaatatgggc ctttacaatg agcgacctgg tggtcaccta caaaactgaa tgatgaacag   5280
tagtatcact agtagtgagg caatcagacg tatgtacttc ttggcatggt gcaagaagta   5340
ccaagcactg cctgagaaat ctgccaaaaa tgttcgctag aacctaatca agacctggat   5400
tccagtttat gggaaataga ggaaatagag gaacaaaaat gtactgtgaa gaaataatca   5460
gacaaatcca gaatgtgggg agtactatag gacagctggc taattcgttc aaaaaccaat   5520
gtcaaagaac aaaaatcagt atcattaaga aaaaatatgg aaagatgatt ctaagctgag   5580
acaaaaagga tagcaaaagt aatgcagcca atacatctta attgggcaaa agtgattaat   5640
aacattatga tacaatggaa aaaaattaac ataggttgag tatctcatgt tattaaggat   5700
ttattataaa ctagatgtga tgagaaacat ttagtaacca tgataagaga atgtcatatt   5760
ggaagataca gcatttttgg catgaagtgt cataatatag gaaatgtaga aatggttcac   5820
tcaaacatga tagttgagag attaaatact aaaagatgat agatagatag acagataata   5880
ggaagatagt agatacatac atacatacat acttagatac atagatagat acatagatac   5940
ataaagaaac agatgataga ttagatagat agatagatag atagatagat agatagatag   6000
atggatagat agatggatag atagatgcag gtataataca acagttttca tttctgcctt   6060
ggcaacattg atctaatttt aaagtgctct catgttgctg tctttcttca aaatattcaa   6120
```

```
taacttagaa tgaaagttca attgactaaa attaaagaac tatttcaaat attttcaggt   6180
acaacatgga tgcatgaaat tttagacatg attctaaatg atggtgatgt ggagaaatgc   6240
aaaagagccc agactctaga tagacacgct ttccttgaac tgaaatttcc ccataaagaa   6300
aaaccaggtg agtaatatgc acgaagatag aaaggacttt cacttcagga ttccagagca   6360
atgtgtactg tctctgatag agcatccgtg gtagccagaa gtagcctgta tctttcatga   6420
ggtctatttg ttctcaggcc aacaatcaaa ctctagattg ggtcttcagg gcttcctcct   6480
gttcttagct ggtggccttt atctccccaa taagattttc attctctttc tcatatttct   6540
cctacccaat gttacgataa agaagactcc ctctgctttg tattctcctt catatgtttg   6600
aatcagtgga aaggccagaa attagcaatc agctattgta aaataacagg tgtgatttct   6660
gaagaaaaag gaggagaagt aggggggata taccgtggac attcccagaa ttaattgggg   6720
gagctgaaaa ggtttcctca gagtgtaaaa cccagtgaat aacatgaaat aaagacagac   6780
ctcctagagg tctttctttc caagaatgac aacctattgt aaaaaaatgg atgtaatttc   6840
tgacaaacaa aagagagaga gaaaaagaga aggaaaaaa acaaccagat ataacaaa    6900
cattcccaga attaatcgag ggtgaaaaag agctttcctg aaagtctaaa agctgagaga   6960
ataagaggaa ataagcaaaa ctctcctaga aggttaggca ggattggatg ctttgtatgt   7020
ccttgtggat aaaaaattac tatttccaat ggatataaaa caaatataaa tcactctaca   7080
gacaaagata taaatggaat tcaagtattt tggcagagtg ccaagaataa acaaagaata   7140
taaattgttt cttgctagat ttggagttcg ttcttgaaat gtcctcacca caactgataa   7200
aaacacatct cccttcacat ctgattccac catctatctg gaaagaaaac tgcaaggtat   7260
aaagagggg cttttcaaac ttctcttagc ttggtgatat aaactataca actgaagata   7320
tcttcaaaa taatatactt tgaaaaatat tttccaaaat ataatttgct attttcctta   7380
gatgaagcac ttaaaatcaa ggattacata aatttgaaat ctgcaaacat ccatgttttc   7440
taaaattcat tttcctctaa tcctatttca tgaaaaattc ttggtaagat tttccaaaat   7500
tgagtctgtg ttgctacaaa tcagagagtg tattgggagc tagaatggag ggaaacacat   7560
ttaaaaataa aaccctgttg ctttgctctg ccaaagtact agaagatatt ctcctggcct   7620
cagaagcaga ggtatagaat ctgctcttgt caaggcttcc acacctccat aatctactca   7680
ataaactaag ctcaaacctg tcctcatttt tatccccctc acctctatgt ctgatctgtc   7740
acaaagtcca gttcattctt cccatccttc taatctgtgc actacactgc aacactacca   7800
cctgtaccca actcagctca ctgctctctt ttgcctccca ctttgtcagc ctgcctctag   7860
acctgccccc tccaacccct cctccctgta acctctactc ttcctaaaac acaatctgac   7920
tgaggtattt ccccactata aacacttcca caggtggacg aagatgcctc catatcctct   7980
atatgacttc catgcccttg acagtctgca ccctgctcca tctcctcccc agggtcttcc   8040
catacctgat cctcactaca gtcctcctga atcctgcag gtccttttcac acatggagca   8100
tccccacacc ttccacatgc tctcatctga ctcaagcatc tcctcatctt tacttgcata   8160
attcctactt gttcttctgg tctttttcata gagggcccct acaggaagct tctgtgaccc   8220
catggctgag tgagtttcat gtatctatat tggggtatct gtgcatgtgt ttccccatca   8280
ttttgttcac cacattgcat tataattttc tctcttctta cctcactgat cagactgtga   8340
gctcctgaca ggcagggact tgatcgtgcc caatttgtca aggtaaacag tgtctggcac   8400
gtaggaaagag ttaacatctc tgttctgcat ttgttgactg aatgatactg aatttccaat   8460
catcacatca ccatgcccct ctgtcctaac catgtgagat atgtgtgtgt gtgtgtatat   8520
```

```
atatatgtat gtatatatat gtatatatgt atgtatgcat acatatgtat gtatatatgt    8580
atgtatgcat atatatgtat atatgtatgt atgcatatat atgtatatat gtgtatatat    8640
acacatatat atgtgtgtat atatatagca aaatcactca aatctttgag aaccattgtc    8700
tgaaacattc ctcatgtgag tctcatacaa atatcaagga actagctctg gactcagtgt    8760
cccaattttt gtgaccaggc atgacccact cgtgtactaa gcatggatta gtggtagtgc    8820
ctccaatcct ctgaaggtca tttacttctt ctgttgaagg ataacaccta ttctctcctt    8880
acctaactct aatcctaata ggagccaaat gagatggtat gcacaaaaat gttttctcac    8940
tctctagtat ttcccctgtt gtaggaatct ggaaaatttc tctcaactca ttgagacaca    9000
gctgaaactc accatttcat ggcccattcc ctgaatgccc aggaatgctt tgtcactggc    9060
tccatgatta ctcagcatat cacatcatat tccatgattg acagtgctgt cctaataatg    9120
tgttcatctt cctgcataac caggaagagt ggttcctcat aaccactctg aagtggggca    9180
ctctcatttg tctttgtgtt ctccatgggt atgagggttg cagagtcaaa aagactccat    9240
ttatttaatg ttttaattca taactaatgt atctaatgct ataaacttat aggatatggt    9300
taccattgta ttgaaacact cacttgagta tttcatgtca gtctattttt ctctccatgg    9360
cttccttccc tctccttgat ttcagattgt ctatgtggcc agaaatccca aggattgcct    9420
ggtgtcctac taccactttc acaggatggc ttcctttatg cctgatcctc agaacttaga    9480
ggaattttat gagaaattca tgtccggaaa aggtgagttc aaactgatct ttttggtacc    9540
ctctttcagg tgactctaac aataagcacc tctgtaaact ggaggagaaa gttacaaaag    9600
gccatcctga ttgaggaggt cctatcttga tgatctggga ctggagaagc caggtagaag    9660 aggtatttt ccaaaattga gtacaaatgt aaattgaggt caactggggt cataagtttt    9720
gagacaaagg taaaagccc caaatccttg acttgagttt caaacaatca acttcaaaat    9780
aagaagaggc aacatttcct atggaaagac ctggcagtgg gaaggcatga gatgatatcc    9840
tgcggtttca tcttgcagtg tgattggatg ccagaccac cacgtatagt tacaaaagtc    9900
atacactgca cagccacaga cagccttttcc cgtaggtcac agtgcacaat cttagacctg    9960
ttcacctgca ggaacctcac attagaatta gcagccatga cccctcatcc atttattaag    10020 atcacaccttt ccagagaagc agtgaacaca ttagggccac acttttcaaa atagcaattg    10080
actagatttg accaggtgtc aaatcagatt ggcaaggatc tcaaacccctt cacagaagaa    10140 gaatatctca tgaaaacaac aatctctaga cagaagaaag ataagatggc tacataaagt    10200
gatttaggat gtaaggacca tcttttacata tttgtatgag cattaatgca gaaacatgat    10260
tatagtattt cattataact gcagtgagca gaacctagac aaatggataa acattacatg    10320
gtgtctccac catttcacta acgtctctca aataattaga acttccataa gtgaaatggg    10380
tgagttgtga tgctgagagc tcccagtcct tgagcaacct aactatccct gagcaagtgt    10440
gttagggacc tgagcttcat tataaccagt cctgacatat tcatattcat attctttga    10500 ggaaaaagaa aaatcaaaat gaagtgactt ccacaacatg acctgaataa aaacagatat    10560
ctgtggaaaa gtcaataaat aataatttcc atcaagcatg tctctccagt gaatcaagag    10620
agataacctc attagaacat tttctctaga aacataaatt aaaaggact acagatgga    10680 aataagaaaa atagcaaatc tagataggac tccaggtgaa tagatttcca atatttatgc    10740
agagaagttt tgagagcagg aaaagtagga ggaagcagag gaagacagga tccaagcttc    10800
ttttcttata tgatttttc caaggcctac attttgttac tgtttttttg tgtcaacttg    10860
```

```
gctggattgt gacacctaca tatttaatca aacaacaatc ctgttgtttc tgtgaaagtg    10920
tcaattgtgt agttgtgatt tacatctata atcagttgac tttaagaaaa ggagataatg    10980
ttaaatatta ataatatggg tggtctttat gcaatcacct gaaggtctta agagaaaaaa    11040
aactcaggtt tccaaaagaa aggattctgc ctcaaggctg ttatatcaaa tcttgcctga    11100
ttttccagca tcccctacag atttaaaaca tgccaagacc cacaactgca ggagccaatt    11160
cctttaaata aaccatatat acataatata cattatatat gtacatttat ctatatgtac    11220
atattacata gccattgcct aaaataaatt atatgtgtac acatttatat tatgcatata    11280
tataaaacat gcacacacat acatatacat ggatgagtcc cctttatact tggtttccct    11340
ttctgcagtt ttagtcaccc acaatcaacc ccaatccaaa aatattacag tatttcaaga    11400
gaaagaagga tagagagagg gagattacat tcacatagat gtaaatatat tagagaatat    11460
tgttatagaa gctctgtttt attattagtt ttgttgtaat tcactcacag tgcctaatat    11520
aaaaattaaa gtaatataca catctatgta taggaaaaaa cataaacact attatcatat    11580
aatttggtac tatctgtggt ttcaggcatc cgctgggggt catgtgatat atcccctgtg    11640
cataaggatg aactaatgta ttctttggat ttgcctattg ctctgtgtct ctggagaacc    11700
tggctgacac agataccagt caccatgaca catgccaaag ttcaagtcac tgcaaactta    11760
catctctgtt tgtcctgatt caaaagagag catttcacac acttgctcac ttggtctgtg    11820
gtcattttcc tctggagaat gttttccatc atccttcaga cgaatcttca agtccactta    11880
gcacaatgct tgcaacatag ctcaccctga ataaagatag ctcctgtgtt tataatgact    11940
gcccagaacc aaaccaggaa gctgccagaa gttacaacct atcagggaca ctaaaacatc    12000
cctgggataa aatatggtgc tggctaactc aggtgtccac tcattctctt accaactagt    12060
gaaaagaaaa tgcatcccat gtttaccacg tagacacagc ctcagctgga aatagaagtt    12120
ctcctggagg gcacccctct ttctgctgct gctgagtctc ttttggaaga ggaacttgca    12180
aactgcatag tgcagctata caggaaaagc agcaggagga ccctacccat ttataggatg    12240
gcctgaatta gttgagtctg aaactaaaca tggtttacca ggaacagggg aagaattta    12300 ttgccgaatg ttttaagaca tgtcacaaga catagtcaat gtgtgcaaag tcacatataa    12360
taaatgtgta ctataaatct cggctttaca ccatatagac aaattttatt actagaaaat    12420
tatttccact tcgttaagga accagaacga tagttacaga agcttattc aaaggagcac    12480 taatttactt tatagccttg ggttttgtcc cagtactggg aactaacagt gctctgactt    12540
cttccagttg ttggcgggtc ctggtttgac catgtgaaag gatggtgggc tgcaaaagac    12600
atgcaccgga tcctctacct cttctacgag gatattaaaa aagtaagtgg cactgagact    12660
tataggtcag acccagaaac cctcctgaca atgttattct gttaaaaagc tgtgtctta    12720 attggccaag ttcttcttct ttcctccctc ttcacaatgc cttttctcc catgatcaga    12780 atccaaaaca tgagatccac aaggtgttgg aattcttgga gaaaacttgg tcaggtgatg    12840
ttataaacaa gattgtccac catacctcat ttgatgtaat gaaggataat cccatggcca    12900
accatactgc ggtacctgct cacatattca atcactccat ctcaaaattt atgaggaaag    12960
gttggtggca tttctttcc ttaactgaac tctaaaaaat tttctaccct atatgctaaa    13020
ataattttca acctaatttt caggcagaag tgactcattt cagttaaatt ttgaatctct    13080
gctcccttca ccctgcctgt ttgcagacag ccaatgtcag tggttctgaa acttgagtca    13140
cattagaacc cctgcaggcc ttgctaaagc tctgattgct ggtccccact cagagatact    13200
gattccacag atccagcagt agccctcaaa tttgcttttc tctcaagtac tcaggtgatg    13260
```

```
ctgatggtgc tggtcacttt gattacaata cccacctcaa ccatgaactt cccttttgaag  13320 gcttgtgcat cctctgagca gctttgaaca ctcatcttta gtctatccct gtagttcaaa  13380
accctagcta agcacttagt acttggattt gtaactactg atattcatgt ctgtctccaa  13440
aataagatga taggctgtcc tgaagagagt gtagtgttca gttttgttcc actagaacct  13500
agtatagaga ctcatacctc aaaacaactc agtaatggcc tgttgtgtga gtgtacagat  13560
gaatgaacat tatttctgtc ctcaacaagt taacattcta gatacatgca aaaatagctg  13620
caaaaagtta taaacaagaa agtaaagtgg aagctatact aggaattccc taataccagt  13680
tctcctggct gtatcaaaat tacctttaaa aacagtgacc ccattccaga acattccaat  13740
taactagttg caagctggaa tctagaattt gatattatgg gcaagcattt cagattaatc  13800
ctcttgtcaa agggtaggaa accagtagaa ataaagtact aggataactt agagaaacaa  13860
ttcattagta cagcatttgt tgggctgaca aggtacaaca gtttgcagaa gatccctagt  13920
atccaaatgt catttccagt ggatttacta tttaatttta cccaacaagt aatatcttct  13980
acaatgaggt tactgacatc ttgtaacgtc tttcactgtc cctgggagaa taagataggc  14040
tgtcccccag gaagtccatg atggtaacca gctgtagact ttgggttggg tacactagag  14100
ccaggagtgt accctggagc agaagattca gcacagtggg gcacctcagt ggggcctgca  14160
gcatttgagg aaggagtata aggatgctgt gtgccttgtg gtaagaaagc caagtggagt  14220
ggaaatgagg gaccattcat agtggaaaga ccagagggag tgggactgag ggaccctcac  14280
tcatgggaaa atcacgtggg taggcctagg aaccattcac tatagaaagg ttaggtggaa  14340
tgggtgcaga gtctgtcatg aacttctttg atgtcctaca gggatgcctg gagactggaa  14400
gaaccacttt actgtggctt tgaatgagaa ctttgataag cattatgaaa agaagatggc  14460
agggtccaca ctgaacttct gcctggagat ctgagaggaa caacaacaaa ctaggtgaca  14520
gagactatgc caactatttc gcctttgatt ctgttgagca aggaactgtg actgaatgtg  14580
gagcttatga gcttcagtcc atctcctata gtgtggctag tttgctataa tattaaaaca  14640
tgatttaaaa tatcaacaaa ccagttactc cagtaaataa aataagagaa ttagagagca  14700
gagtccgcct acatgagttt ttttgtttgt ttgtttttta agtacaggta tgttttattg  14760
tgcatgacag acagagcaaa aacaaacaat tgcatcatgg attcccatgt gtgatcccaa  14820
gtagatttca caagaaaatt atgcataggt attacaagcc ccattgttaa gagagaatgt  14880
aacagcttga agtgtacatt ctatacttt atgtataaat aataacttcc aagagaaaag  14940
agctgataag tacatttcag agtcaccatt tctgtaatag aatgatataa aaataaatta  15000
ctactgcaaa atatcaatca attgcaaaat gattactgct ctacttttgg cttgtaacta  15060 atttttctcaa tcgaaagagt ttgagttgga gaaattagtc agtgagtact cctgtaaaaa  15120
atcttcccac gatataaata aaatgcttaa tgtatctaat ctataaattg agatctggga  15180
caaatgcacc atgactatgc attgccattc tcttaataac tatgcattgc cattctctta  15240
ataaagagtc tctgttgcat cactctaaca ataggtatga cctcagattt aatataaatt  15300
tagtgcttca accatgcacc agtgaagacc tggttttta tatgaccaag tacaattgtc  15360
ttattagaag agaaggtcct gaggggcctt agggagtagg tggatgccaa cagggctgat  15420
ggcctcagag atgacagcat gtaacatgta agaaggggg gaaatttgga aagacttaaa  15480
ctcagaaata aaattaaaga agtgtaaaaa ggtattcaat taacatcttg aaagggaatc  15540
aggaacaata tacatagctc ccagtacaca gagcaaagta acctcccctgt ggttgtgatc  15600
```

-continued

```
attgtctcta ccttatcgta gtgacaaggc agtgctattg ttacgccagg caaaggggaa   15660
atgacatcct attctctagt caactggatg gaagacaaac tcaaaggtaa aaaatagatg   15720
atgagatttt aagaaaagag agcagctggt ccctaaggcc tgctgtaagg aagcagagag   15780
gatgaagatg ggggcatttg aaccagccca gaggggaccc tggggtgaaa gttccccatc   15840
aggcattacc ccactgccta catccagcca gataacccaa ccacctgaat taccatcctc   15900
atatttagtt ggtgatccag agaagagatt tcctctagta ttccctaaag gtatagcaag   15960
aaaaaaagag attccttgat cactcctgcc tagtcaatgc actggaagac tggttcacag   16020
ggctactgtg ctttgtaatt ggagacatga gaatccacaa tgattagaaa gctcgggccc   16080
caggtactgt cagagtccac agtctacctc agagaggagg aggcagatta aaggaaaagc   16140
aaatttcatt ttcctactca gaaatgattt tctactaatt gaaaagcaat tgaatgctgt   16200
caataaagac atttcctgta ctaaccttgg actcagagta ttgatgacca actatacaaa   16260
gcttatttct tccatgcaat ggatgatacc tgcctgcctt tgcaggtatt aaggggtatg   16320
atgctgagag tccaggtgta gaagatggga tcacgggttt tgggcaaagc attttggcta   16380
tctaatgtta agaactgtaa ggtttgagaa tgccttgatg aaagttcgta aaagctacaa   16440
acagagttgc tggtcatttc tacaaggagg ctgtgaactg ctcttcatct tctagaggca   16500
tattttggct atgggctact aagattcaga caggtgtaag atatagtttg ccccatggcc   16560
tcccctagaa ctttccccaa tgtgactgtt cctggactaa actgagggtc gggctgctat   16620
ttcctgtggc ccaataacaa gatgcagatg aactgggggag gaagagaagt tttatttctg   16680
taactggtta cattcagagg gcctggaaat tatcaccaaa ccaactcaaa atgacaaaat   16740
ttttcagagc ttatctacct tctaagctgt atgtctacat gtaagtgtgc atgccttcta   16800
aagacatatg tgattaattt attttaattt ataactaaga tctgagtcct gaagaccttc   16860
ctctggtgcc taatgaagtt tgcttaattt aaatgggtct ccaggtactg ggttgatcac   16920
ccttatcttg tctcctgtta aactactgag gtttgggggag ttccttcaga cctccaataa   16980
acgtgtttgt ggaggcctgg ggagtttctt cagagcccca ataaaactta tataatccta   17040
actgggtact gttaagaact cctttattat tttgtcatgt tgtaaggccc aggaaacgcc   17100
taggcaaaac tctggatggg cttttgttac atttcagcct ttgcataagg gcactggctt   17160
tttttaatat ttaacttaac cactcactga atactgaaac agttgtgatg gaggcctgca   17220
ttaatgcaac ctgcctgcca caatccccac tgtcaatttg tgcataattc ttatcatgct   17280
agtatattta tttatcatga gaattgtagg gatatggggc attgtaatat ttctggctac   17340
ttcctgctga gtgagtgtca ttgttatggg acactgaatg cagcattggt ataggggagg   17400
tctatttgtt cccagcagca ctctttgttt caggggctta gaggcagcac ctgctgaaac   17460
atttagtctt cagttcacag ggctttaaga aagcacaact taggtttcag tgatttccag   17520
ttaggaaaaa tgggggtagtg catgggcttt catgcagaag agccttcagt gcaagtccat   17580
gacaatgttt gcaactcagt tttatcctca aaagctctaa ctacttttc ggtattctaa   17640 atctgctttg cttttaattca gttttcaaaa tattcttctt cctcaggaaa tagcacatgc   17700
tttatagttg aatgaatctg ttggctcctg gcacttgtaa gccagatatc tttatctgca   17760
aaatggtatc atatctatct catgagatca ttgtaaagat ttacactatc atacttgtaa   17820
agtgtacata gttgtgttca agaaatttag cttccttctc cctcttgcac acctcaaccc   17880
cacatcataa agcaaagttt aatccatata aacactggta ggattagtcc cacatattgg   17940
gacagtggac tgatttctga atttcaaacc atcgtgtctg agtgtctgca caaattcact   18000
```

```
ctcatgaccc agtgcatcag catcctagaa ttacaaaact agcatctgag atgtcctcag    18060
aaatttaatc aaaagctata gctttctctc tttctgtatc tctttgatca aaaagatcca    18120
agaaataagg atctatgctt ctgggtcaac ttgagattcc ttttattcct cctcttagtg    18180
accttctgtt aagttcatag gttctttttg ccatctgttg tagtccaaat actagagtta    18240
gttatactat gcttcaccac caacattgtt cctccttcac acagcctttc ctgttctccc    18300
ccaggagata tcattgctcc ttcccaccaa atctcctggc actctgtctg tacgtaggca    18360
gcatgtactt tctcagccag ccttgtgatt gtttgtgttt atgcttaatt cctttccttc    18420
aaggtaagcc tcttgagggc agggacaacc ctcatctttg tgttgctaca gtatctggga    18480
cagtacagtg tctggcacta ggagtcactt gagaaatatt tttaaaatgt gttcaaatga    18540
tcctttaact catttctctc caaatactgt ccaaatggaa catcatcccc aagggaagac    18600
ccaacatgat ttgtttggtg tgactgttcc acatacagga cccaaagcgg gaaattgaga    18660
agatactgaa gttcctggaa aaagacatat cagaggaaat tctgaataaa atcatctatc    18720
acacctcctt tgatgtaatg aagcaaaacc caatgaccaa ctataccact ttgcccacca    18780
gcattatgga ccactccatc tcccctttta tgaggaaagg tagataagct ttgtagtcta    18840
agatgtcaaa tggaactctg tggtccccat ggtctgctta gattttccag taatgtttca    18900
ttctccatta tttattcttt ccagcagcac cactgtacaa cctttgagag gcaagttgcc    18960
tgtttctcct cattcttggt ggggtcctaa gggtgcatgc ttacctctcc ctctactcct    19020
gcagcaatca ttaagatttt gccttgtttc agggatgcct ggagactgga agaactattt    19080
tactgtggcc caaatgaag aatttgacaa ggactaccag aagaagatgg caggaagcac    19140
cctaaccttc cgcacagaga tctgagagca gtcagggagt ctgtcctgga ctttcttacc    19200
agatttttgc catttgagcc tcatgatcaa ggacacttaa acaaagaca cccttcctcc    19260 agtctggagc tgttacacac tacctgtaga tgataatact tcatcaaaat gtaaccaaat    19320
cctgggtaga gttttttaatt aagatacatg atccctcatt tagacaccaa ccacataacg    19380
tactcccctg tcctaaggca aaataaaggc aatttagttc catcactagt ttacaatagt    19440
gaaataaata aagagataaa taagagtaga atttcaatgt aagagaaagt gagcaagaga    19500
agaatgagga tgataagtgg gcactaagga taatgtgtgg gggaactggt ttttattttt    19560
aaaggtcagg aatgagaggc agaggatagt cctactcttg aagatattag attaggaggt    19620 gcaggggggtg gcatgaagga tggaatgctg tgagctgggt ctggctcagg tggcttcaag    19680
ctgaaatggt cccaaaacca aagagaaagg ccacaggaga gcgataagga acacaagatg    19740
aacaagaaac tcagcctact tctgtggcca acacaaggct ggaaagcaga gaaagatttt    19800
atctttcaga tggacttctg agagagagag gaagtcttca gtgagctcaa gggaaaaata    19860
aaataaaata tttggtaact catggacgtt aagaaaagct taaatttcac atctctgtgg    19920
aaaatcgttt tttatacttt tttttaaagg gctcttagca aaactgtcag cattgccaag    19980
ttcttcagct acactaatga ttatgttctt ttccttcttt ttgttaaaac ctgtaccaag    20040
aaaatatctg ccatcatttt atacaagcta tacaacgatc catgtatcat tattctttta    20100
atgtcaggaa ggtacatttt gtgggatagg tggttaactt atcattaaac catacaacac    20160
aaaaa                                                                20165
```

<210> SEQ ID NO 8
<211> LENGTH: 283
<212> TYPE: PRT

<213> ORGANISM: Homo sapiens

<400> SEQUENCE: 8

```
Glu Val Asn Gly Ile Leu Met Ser Lys Leu Met Ser Asp Asn Trp Asp
1               5                   10                  15
Lys Ile Trp Asn Phe Gln Ala Lys Pro Asp Asp Leu Leu Ile Ala Thr
            20                  25                  30
Tyr Ala Lys Ala Gly Thr Thr Trp Thr Gln Glu Ile Val Asp Met Ile
        35                  40                  45
Gln Asn Asp Gly Asp Val Gln Lys Cys Gln Arg Ala Asn Thr Tyr Asp
    50                  55                  60
Arg His Pro Phe Ile Glu Trp Thr Leu Pro Ser Pro Leu Asn Ser Gly
65                  70                  75                  80
Leu Asp Leu Ala Asn Lys Met Pro Ser Pro Arg Thr Leu Lys Thr His
                85                  90                  95
Leu Pro Val His Met Leu Pro Ser Phe Trp Lys Glu Asn Ser Lys
            100                 105                 110
Ile Ile Tyr Val Ala Arg Asn Ala Lys Asp Cys Leu Val Ser Tyr Tyr
        115                 120                 125
Tyr Phe Ser Arg Met Asn Lys Met Leu Pro Asp Pro Gly Thr Leu Gly
    130                 135                 140
Glu Tyr Ile Glu Gln Phe Lys Ala Gly Lys Val Leu Trp Gly Ser Trp
145                 150                 155                 160
Tyr Asp His Val Lys Gly Trp Trp Asp Val Lys Asp Gln His Arg Ile
                165                 170                 175
Leu Tyr Leu Phe Tyr Glu Asp Met Lys Glu Asp Pro Lys Arg Glu Ile
            180                 185                 190
Lys Lys Ile Ala Lys Phe Leu Glu Lys Asp Ile Ser Glu Glu Val Leu
        195                 200                 205
Asn Lys Ile Ile Tyr His Thr Ser Phe Asp Val Met Lys Glu Asn Pro
    210                 215                 220
Met Ala Asn Tyr Thr Thr Leu Pro Ser Ser Ile Met Asp His Ser Ile
225                 230                 235                 240
Ser Pro Phe Met Arg Lys Gly Met Pro Gly Asp Trp Lys Asn Tyr Phe
                245                 250                 255
Thr Val Ala Gln Ser Glu Asp Phe Asp Glu Asp Tyr Arg Arg Lys Met
            260                 265                 270
Ala Gly Ser Asn Ile Thr Phe Arg Thr Glu Ile
        275                 280
```

<210> SEQ ID NO 9
<211> LENGTH: 283
<212> TYPE: PRT
<213> ORGANISM: Homo sapiens

<400> SEQUENCE: 9

```
Glu Val Asn Gly Ile Leu Met Ser Lys Leu Met Ser Asp Asn Trp Asp
1               5                   10                  15
Lys Ile Trp Asn Phe Gln Ala Lys Pro Asp Asp Leu Leu Ile Ala Thr
            20                  25                  30
Tyr Ala Lys Ala Gly Thr Thr Trp Thr Gln Glu Ile Val Asp Met Ile
        35                  40                  45
Gln Asn Asp Gly Asp Val Gln Lys Cys Gln Arg Ala Asn Thr Tyr Asp
    50                  55                  60
Arg His Pro Phe Ile Glu Trp Thr Leu Pro Ser Pro Leu Asn Ser Gly
```

-continued

```
                65                  70                  75                  80
Leu Asp Leu Ala Asn Lys Met Pro Ser Pro Arg Thr Leu Lys Thr His
                    85                  90                  95

Leu Pro Val His Met Leu Pro Ser Phe Trp Lys Glu Asn Ser Lys
            100                 105                 110

Ile Ile Tyr Val Ala Arg Asn Ala Lys Asp Cys Leu Val Ser Tyr Tyr
            115                 120                 125

Tyr Phe Ser Arg Met Asn Lys Met Leu Pro Asp Pro Gly Thr Leu Gly
            130                 135                 140

Glu Tyr Ile Glu Gln Phe Lys Ala Gly Lys Val Leu Trp Gly Ser Trp
145                 150                 155                 160

Tyr Asp His Val Lys Gly Trp Trp Asp Val Lys Asp Gln His Arg Ile
                    165                 170                 175

Leu Tyr Leu Phe Tyr Glu Asp Met Lys Glu Asp Pro Lys Arg Glu Ile
                    180                 185                 190

Lys Lys Ile Ala Lys Phe Leu Glu Lys Asp Ile Ser Glu Glu Val Leu
                    195                 200                 205

Asn Lys Ile Ile Tyr His Thr Ser Phe Asp Val Met Lys Glu Asn Pro
            210                 215                 220

Met Ala Asn Tyr Thr Thr Leu Pro Ser Ser Ile Met Asp His Ser Ile
225                 230                 235                 240

Ser Pro Phe Met Arg Lys Gly Met Pro Gly Asp Trp Lys Asn Tyr Phe
                    245                 250                 255

Thr Val Ala Gln Ser Glu Asp Phe Asp Glu Asp Tyr Arg Arg Lys Met
                    260                 265                 270

Ala Gly Ser Asn Ile Thr Phe Arg Thr Glu Ile
            275                 280

<210> SEQ ID NO 10
<211> LENGTH: 283
<212> TYPE: PRT
<213> ORGANISM: Homo sapiens

<400> SEQUENCE: 10

Glu Val Asn Gly Ile Leu Met Ser Lys Met Met Ser Glu Asn Trp Asp
1               5                   10                  15

Lys Ile Trp Asn Phe Gln Ala Lys Pro Asp Asp Leu Leu Ile Ala Thr
                20                  25                  30

Tyr Ala Lys Ala Gly Thr Thr Trp Thr Gln Glu Ile Val Asp Met Ile
            35                  40                  45

Gln Asn Asp Gly Asp Val Gln Lys Cys Gln Arg Ala Asn Thr Tyr Asp
50                  55                  60

Arg His Pro Phe Ile Glu Trp Thr Leu Pro Pro Leu Asn Ser Gly
65                  70                  75                  80

Leu Asp Leu Ala Asn Lys Met Pro Ser Pro Arg Thr Leu Lys Thr His
                    85                  90                  95

Leu Pro Val Gln Met Leu Pro Ser Phe Trp Lys Glu Asn Ser Gln
            100                 105                 110

Ile Ile Tyr Val Ala Arg Asn Ala Lys Asp Cys Leu Val Ser Tyr Tyr
            115                 120                 125

Tyr Phe Ser Arg Met Asn Lys Met Leu Pro Asp Pro Gly Thr Leu Gly
            130                 135                 140

Glu Tyr Ile Glu Thr Phe Lys Ala Gly Lys Val Leu Trp Gly Ser Trp
145                 150                 155                 160
```

```
Tyr Asp His Val Lys Gly Trp Trp Asp Val Lys Asp Lys His Arg Ile
                165                 170                 175
Leu Tyr Leu Phe Tyr Glu Asp Met Lys Glu Asp Pro Lys Arg Glu Ile
            180                 185                 190
Lys Lys Ile Val Lys Phe Leu Glu Lys Asp Ile Ser Glu Glu Val Leu
        195                 200                 205
Asn Lys Ile Ile His His Thr Ser Phe Asp Val Met Lys Gln Asn Pro
    210                 215                 220
Met Ala Asn Tyr Thr Thr Leu Pro Ser Ser Ile Met Asp His Ser Ile
225                 230                 235                 240
Ser Pro Phe Met Arg Lys Gly Met Pro Gly Asp Trp Lys Asn Tyr Phe
                245                 250                 255
Thr Val Ala Gln Ser Glu Asp Phe Asp Glu Asp Tyr Arg Lys Lys Met
            260                 265                 270
Ala Gly Ser Thr Ile Thr Phe Arg Thr Glu Ile
        275                 280

<210> SEQ ID NO 11
<211> LENGTH: 52
<212> TYPE: DNA
<213> ORGANISM: Homo sapiens

<400> SEQUENCE: 11
ttagtattga tcttacccat cccagattcc cmatggcgaa gattgagaaa aa          52

<210> SEQ ID NO 12
<211> LENGTH: 57
<212> TYPE: DNA
<213> ORGANISM: Homo sapiens

<400> SEQUENCE: 12
gcaacattga tctaatttta aagtgctctc atuttgctgt ctttcttcaa aatattc     57

<210> SEQ ID NO 13
<211> LENGTH: 46
<212> TYPE: DNA
<213> ORGANISM: Homo sapiens

<400> SEQUENCE: 13 ccaaccccte ctccctgtaa cctctaytct tcctaaaaca caatct                 46

<210> SEQ ID NO 14
<211> LENGTH: 49
<212> TYPE: DNA
<213> ORGANISM: Homo sapiens

<400> SEQUENCE: 14
agcagccatg acccctcatc catttattma gatcacacct tccagagaa              49

<210> SEQ ID NO 15
<211> LENGTH: 55
<212> TYPE: DNA
<213> ORGANISM: Homo sapiens

<400> SEQUENCE: 15
aggaggaagc agaggaagac aggawccaag cttcttttct tatatgattt tttcc       55

<210> SEQ ID NO 16
<211> LENGTH: 52
<212> TYPE: DNA
<213> ORGANISM: Homo sapiens
```

```
<400> SEQUENCE: 16
ccacttcgtt aaggaaccag aacgawagtt acagaagctt atttcaaagg ag          52

<210> SEQ ID NO 17
<211> LENGTH: 62
<212> TYPE: DNA
<213> ORGANISM: Homo sapiens

<400> SEQUENCE: 17
tttaaaatat caacaaacca gttactccag yaaataaaat aagagaatta gagagcagag  60
tc                                                                62

<210> SEQ ID NO 18
<211> LENGTH: 42
<212> TYPE: DNA
<213> ORGANISM: Homo sapiens

<400> SEQUENCE: 18
aggtattaca agcsccattg ttaagagaga atgtaacagc tt                    42

<210> SEQ ID NO 19
<211> LENGTH: 36
<212> TYPE: DNA
<213> ORGANISM: Homo sapiens

<400> SEQUENCE: 19
ttttgtggga taggtgrtta acttatcatt aaacca                           36

<210> SEQ ID NO 20
<211> LENGTH: 27
<212> TYPE: DNA
<213> ORGANISM: Homo sapiens

<400> SEQUENCE: 20
ggtgggaaaa agtmtgtaat ttccaag                                     27

<210> SEQ ID NO 21
<211> LENGTH: 28
<212> TYPE: DNA
<213> ORGANISM: Homo sapiens

<400> SEQUENCE: 21
gtgggctgca aaagacaygc accggatc                                    28

<210> SEQ ID NO 22
<211> LENGTH: 25
<212> TYPE: DNA
<213> ORGANISM: Homo sapiens

<400> SEQUENCE: 22
ggagaaaact tkgtcaggtg atgtt                                       25

<210> SEQ ID NO 23
<211> LENGTH: 20
<212> TYPE: DNA
<213> ORGANISM: Homo sapiens

<400> SEQUENCE: 23
actttactgt ggctwtgaat                                             20
```